(12) United States Patent
Torrens Jover et al.

(10) Patent No.: US 7,553,965 B2
(45) Date of Patent: Jun. 30, 2009

(54) 5-HT$_7$ RECEPTOR ANTAGONISTS

(75) Inventors: Antoni Torrens Jover, Barcelona (ES); Susana Yenes Mínguez, Barcelona (ES); Josep Mas Prió, Barcelona (ES); Luz Romero Alonso, Barcelona (ES); Alberto Dordal Zueras, Barcelona (ES); Helmut Henrich Buschmann, Barcelona (ES)

(73) Assignee: Laboratories Del Dr. Esteve, S.A., Barcelona (ES)

( * ) Notice: Subject to any disclaimer, the term of this patent is extended or adjusted under 35 U.S.C. 154(b) by 56 days.

(21) Appl. No.: 11/813,069

(22) PCT Filed: Dec. 27, 2005

(86) PCT No.: PCT/EP2005/014044

§ 371 (c)(1),
(2), (4) Date: Oct. 10, 2007

(87) PCT Pub. No.: WO2006/069775

PCT Pub. Date: Jul. 6, 2006

(65) Prior Publication Data

US 2009/0036480 A1 Feb. 5, 2009

(30) Foreign Application Priority Data

Dec. 28, 2004 (EP) .................................. 04380280

(51) Int. Cl.
C07D 221/04 (2006.01)
A01N 43/42 (2006.01)

(52) U.S. Cl. ......................................... 546/99; 514/296

(58) Field of Classification Search .................. 546/99, 546/296
See application file for complete search history.

(56) References Cited

FOREIGN PATENT DOCUMENTS

| EP | 0 021 580 | 12/1983 |
|---|---|---|
| EP | 0 076 072 | 5/1987 |
| EP | 0 937 715 | 8/1999 |
| WO | WO 97/29097 | 8/1997 |
| WO | WO 97/48681 | 12/1997 |
| WO | WO 97/49695 | 12/1997 |
| WO | WO 99/24022 | 5/1999 |
| WO | WO 00/00472 | 1/2000 |
| WO | WO 03/048118 | 6/2003 |

OTHER PUBLICATIONS

Terron, J. A., IDrugs, vol. 1(3), pp. 302-301, 1998.
Lovenberg et al., Neuron, vol. 11, pp. 449-458, 1993.
Terron, J. A., Br. J. Pharmacol., vol. 121, pp. 563-571, 1997.
Schoeffter et al., Br. J. Pharmacol., vol. 117, pp. 993-994, 1996.
Terron, J. A., Eur. J. Pharmacol., vol. 439, pp. 1-11, 2002.
De Ponti et al., Drugs, vol. 61, pp. 317-332, 2001.
Read et al., Br. J. Pharmacol., vol. 140, pp. 53-60, Jul. 29, 2003.
Wesolowska, A., Polish J. Pharmacol., vol. 54, pp. 327-341, 2002.
Pelletier et al., J. Org. Chem., vol. 52, pp. 616-622, 1987.
Hodge Markgraf et al. Heterocycles, vol. 29(12), pp. 2399-2402, 1989.
Huffman et al., J. Org. Chem., vol. 36(1), pp. 111-117, 1971.
Grunewald et al., J. Med. Chem., vol. 31(2), pp. 433-444, 1988.
Munson et al., Anal. Biochem., vol. 107, pp. 220-239, 1980.
Vermeulen et al., J. Med. Chem., vol. 47, pp. 5451-5466, Sep. 23, 2004.
European Patent Office, European Search Report for EP 04380280.0, issued May 12, 2005.
PCT International Search Report, PCT/EP2005/014044, dated Feb. 27, 2006.

Primary Examiner—Jafar Parsa
(74) Attorney, Agent, or Firm—Locke Lord Bissell & Liddell, LLP; Brandon T. Schurter

(57) ABSTRACT

The invention relates to compounds having pharmacological activity towards the 5-HT7 receptor, and more particularly to some 2,2a,4,5-tetrahydro-1H-3-aza-acenaphthylen substituted sulfonamide compounds, to processes of preparation of such compounds, to pharmaceutical compositions comprising them, and to their use for the treatment and or prophylaxis of a disease in which 5-HT is involved, such as CNS disorders.

30 Claims, No Drawings

5-HT$_7$ RECEPTOR ANTAGONISTS

FIELD OF THE INVENTION

The present invention relates to compounds having pharmacological activity towards the 5-HT7 receptor, and more particularly to some 2,2a,4,5-tetrahydro-1H-3-aza-acenaphthylen substituted sulfonamide compounds, to processes of preparation of such compounds, to pharmaceutical compositions comprising them, and to their use in therapy, in particular for the treatment and or prophylaxis of a disease in which 5-HT$_7$ is involved, such as CNS disorders.

BACKGROUND OF THE INVENTION

The search for new therapeutic agents has been greatly aided in recent years by better understanding of the structure of proteins and other biomolecules associated with target diseases. One important class of proteins that has been the subject of extensive study is the family of 5-hydroxytryptamine (serotonin, 5-HT) receptors. The 5-HT$_7$ receptor discovered in 1993 belongs to this family and has attracted great interest as a valuable new drug target (Terrón, J. A. *Idrugs*, 1998, vol. 1, no. 3, pages 302-310: *"The 5HT$_7$ receptor: A target for novel therapeutic avenues?"*).

5-HT$_7$ receptors have been cloned from rat, mouse, guinea pig and human cDNA and exhibit a high degree of interspecies homology (approx. 95%), but it is unique in that it has a low sequence homology with other 5-HT receptors (less than 40%). Its expression pattern, in particular structures of the central nervous system (CNS) (highest in hypothalamus (in particular suprachiasmatic nuclei) and thalamus) and other peripheral tissues (spleen, kidney, intestinal, heart and coronary artery), implicates the 5-HT$_7$ receptor in a variety of functions and pathologies. This idea is reinforced by the fact that several therapeutic agents, such as tricyclic antidepressants, typical and atypical antipsychotics and some 5-HT$_2$ receptor antagonists, display moderate to high affinity for both recombinant and functional 5-HT$_7$ receptors.

Functionally, the 5-HT$_7$ receptor has been implicated in regulation of circadian rhythms in mammals (Lovenberg, T. W. et al. *Neuron*, 1993, 11:449-458 *"A novel adenylyl cyclase-activating serotonin receptor (5-HT$_7$) implicated in the regulation of circadian rhythms"*). It is known that disruption of circadian rhythms is related to a number of CNS disorders including depression, seasonal affective disorder, sleep disorders, shift worker syndrome and jet lag among others.

Distribution and early pharmacological data also suggest that the 5-HT$_7$ receptor is involved in the vasodilatation of blood vessels. This has been demonstrated in vivo (Terrón, J. A., *Br J Pharmacol*, 1997, 121:563-571 *"Role of 5-HT$_7$ receptors in the long lasting hypotensive response induced by 5-hydroxytryptamine in the rat"*). Thus selective 5-HT$_7$ receptor agonists have a potential as novel hypertensive agents.

The 5-HT$_7$ receptor has also been related with the pathophysiology of migraine through smooth muscle relaxation of cerebral vessels (Schoeffter, P. et al., 1996, *Br J Pharmacol*, 117:993-994; Terrón, J. A., 2002, *Eur. J. Pharmacol.*, 439:1-11 *"Is the 5-HT$_7$ receptor involved in the pathogenesis and prophylactic treatment of migraine?"*). In a similar manner, involvement of 5-HT$_7$ in intestinal and colon tissue smooth muscle relaxation makes this receptor a target for the treatment of irritable bowel syndrome (De Ponti, F. et al., 2001, *Drugs*, 61:317-332 *"Irritable bowel syndrome. New agents targeting serotonin receptor subtypes"*). Recently, it has also been related to urinary incontinence (*British J. of Pharmacology*, September 2003, 140(1) 53-60: "Evidence for the involvement of central 5HT-7 receptors in the micurition reflex in anaesthetized female rats").

In view of the potential therapeutic applications of agonists or antagonists of the 5HT$_7$ receptor, a great effort has been directed to find selective ligands. Despite intense research efforts in this area, very few compounds with selective 5-HT$_7$ antagonist activity have been reported (Wesolowska, A., *Polish J. Pharmacol.*, 2002, 54: 327-341, *"In the search for selective ligands of 5-HT$_5$, 5-HT$_6$ and 5-HT$_7$ serotonin receptors"*).

WO 97/48681 discloses sulfonamide derivatives, which are 5-HT$_7$ receptor antagonists, for the treatment of CNS disorders. The sulphur atom is linked to an aromatic group and to a N-containing heterocyclic group, optionally containing a further heteroatom selected from oxygen or sulphur.

WO 97/29097 describes sulfonamide derivatives for the treatment of disorders in which antagonism of the 5-HT$_7$ receptor is beneficial. The sulphur atom is linked to an aromatic group and to a $C_1$-$C_6$ alkyl substituted N atom.

WO97/49695 describes further sulfonamide derivatives in which the N linked to the sulphur atom is also fully substituted, for example forming part of a piperidine.

WO 03/048118 describes another group of 5HT$_7$ receptor antagonists. In this case aryl and heteroaryl sulfonamide derivatives wherein the sulfonamide group is a substituent on a cycloalkane or cycloalkene ring which additionally bears an amino substituent. The N linked to sulphur atom is fully substituted.

WO99/24022 discloses tetrahydroisoquinoline derivatives for use against CNS disorders and binding to serotonin receptors, in particular 5-HT$_7$.

WO 00/00472 refers to compounds which are 5-HT7 receptor antagonists. The compounds contain a N-containing fused heterocycle such as tetrahydroisoquinoline.

EP 21580 and EP 76072 describe sulfonamide compounds having antiarrhythmic activity, corresponding to the formula $R_2N(CH_2)_n$—NH—$SO_2R_1$, 5-HT$_7$ activity is not mentioned.

EP 937715 A1 refers to a tetrahydrobenzoindole compound that binds selectively to a serotonin receptor subtype 5-HT$_7$ vs 5-HT2.

There is still a need to find compounds that have pharmacological activity towards the receptor 5-HT$_7$, being both effective and selective, and having good "drugability" properties, i.e. good pharmaceutical properties related to administration, distribution, metabolism and excretion.

SUMMARY OF THE INVENTION

We have now found a family of structurally distinct class of sulfonamide compounds which are particularly selective inhibitors of the 5-HT$_7$ receptor. The compounds present a 2,2a,4,5-tetrahydro-1H-3-aza-acenaphthylen moiety, linked through a straight alkylene chain with a sulfonamide moiety. We have found that the compounds display IC-50 values in the nM range 1-200 nM at human 5-HT7 receptors and exhibit selectivity for these receptors vs 5-HT1A, 5-HT2A, 5-HT2B, 5-HT2C, 5-HT3, 5-HT4, 5-HT5A, D1, D2, D3, D4, adrenergic α1A, α1B, α1B, β1, and β2 receptors.

In one aspect the invention is directed to a compound of the formula I:

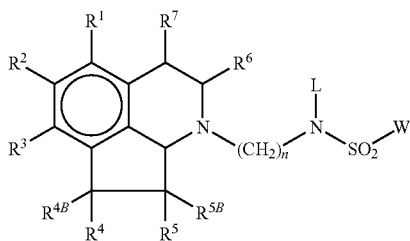

(I)

wherein

W is a substituted or unsubstituted alkyl, substituted or unsubstituted alkenyl, substituted or unsubstituted cycloalkyl, substituted or unsubstituted aryl, substituted or unsubstituted heterocyclyl;

$R^1$, $R^2$, $R^3$, $R^4$, $R^{4B}$, $R^5$, $R^{5B}$, $R^6$ and $R^7$ are each independently selected from the group formed by hydrogen, substituted or unsubstituted alkyl, substituted or unsubstituted cycloalkyl, substituted or unsubstituted alkenyl, substituted or unsubstituted aryl, substituted or unsubstituted heterocyclyl, $-COR^8$, $-C(O)OR^8$, $-C(O)NR^8R^9$, $-HC=NR^8$, $-CN$, $-OR^8$, $-OC(O)R^8$, $-S(O)_t-R^8$, $-NR^8R^9$, $-NR^8C(O)R^9$, $-NO2$, $-N=CR^8R^9$ or halogen;

L is hydrogen, substituted or unsubstituted alkyl, substituted or unsubstituted cycloalkyl, substituted or unsubstituted alkenyl, substituted or unsubstituted aryl, substituted or unsubstituted heterocyclyl, $-COR^8$, $-C(O)OR^8$, $-C(O)NR^8R^9$, $-HC=NR^8$, $-CN$, $-OR^8$, $-OC(O)R^8$, $-S(O)_t-R^8$, $-NR^8R^9$, $-NR^8C(O)R^9$, or $-N=CR^8R^9$; and the pair $R^4$ and $R^{4B}$ or the pair $R^5$ and $R^{5B}$ taken together may form a carbonyl group, t is 1, 2 or 3;

$R^8$ and $R^9$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, halogen;

n is 2, 3, 4 or 5.

or a pharmaceutically acceptable salt, isomer, prodrug or solvate thereof.

In another aspect the invention is directed to a pharmaceutical composition which comprises a compound as above defined or a pharmaceutically acceptable salt, enantiomer, prodrug or solvate thereof, and a pharmaceutically acceptable carrier, adjuvant or vehicle.

In a further aspect the invention is directed to the use of a compound as defined above in the manufacture of a medicament for the treatment of a 5-HT$_7$ mediated disease or condition, i.e. diseases caused by failures in central and peripheral serotonin-controlling functions, such as pain, sleep disorder, shift worker syndrome, jet lag, depression, seasonal affective disorder, migraine, anxiety, psychosis, schizophrenia, cognition and memory disorders, neuronal degeneration resulting from ischemic events, cardiovascular diseases such as hypertension, irritable bowel syndrome, inflammatory bowel disease, spastic colon or urinary incontinence.

DETAILED DESCRIPTION OF THE INVENTION

The typical compounds of this invention effectively and selectively inhibit the 5-HT7 receptor vs other 5-HT receptors such as 5-HT1A, 5-HT2A, 5-HT2B, 5-HT2C, 5-HT3, 5-HT4, 5-HT5A, D1, D2, D3, D4, adrenergic α1A, α1B, α1B, β1, and β2 receptors, Tachykinin NK-1 opiate, GABA, estrogen, glutamate, adenosine, nicotinic, muscarinic receptors and calcium, potassium and sodium channels and neurotransmitter transporters (serotonin, dopamine, norepinephrine, GABA).

In the above definition of compounds of formula (I) the following terms have the meaning indicated:

"Alkyl" refers to a straight or branched hydrocarbon chain radical consisting of carbon and hydrogen atoms, containing no unsaturation, having one to eight carbon atoms, and which is attached to the rest of the molecule by a single bond, e.g., methyl, ethyl, n-propyl, i-propyl, n-butyl, t-butyl, n-pentyl, etc. Alkyl radicals may be optionally substituted by one or more substituents such as a aryl, halo, hydroxy, alkoxy, carboxy, cyano, carbonyl, acyl, alkoxycarbonyl, amino, nitro, mercapto, alkylthio, etc. If substituted by aryl we have an "Aralkyl" radical, such as benzyl and phenethyl.

"Alkenyl" refers to an alkyl radical having at least 2 C atoms and having one or more unsaturated bonds.

"Cycloalkyl" refers to a stable 3- to 10-membered monocyclic or bicyclic radical which is saturated or partially saturated, and which consist solely of carbon and hydrogen atoms, such as cyclohexyl or adamantyl. Unless otherwise stated specifically in the specification, the term "cycloalkyl" is meant to include cycloalkyl radicals which are optionally substituted by one or more substituents such as alkyl, halo, hydroxy, amino, cyano, nitro, alkoxy, carboxy, alkoxycarbonyl, etc.

"Aryl" refers to single and multiple ring radicals, including multiple ring radicals that contain separate and/or fused aryl groups. Typical aryl groups contain from 1 to 3 separated or fused rings and from 6 to about 18 carbon ring atoms, such as phenyl, naphthyl, indenyl, fenanthryl or anthracyl radical. The aryl radical may be optionally substituted by one or more substituents such as hydroxy, mercapto, halo, alkyl, phenyl, alkoxy, haloalkyl, nitro, cyano, dialkylamino, aminoalkyl, acyl, alkoxycarbonyl, etc.

"Heterocyclyl" refers to a stable 3- to 15 membered ring radical which consists of carbon atoms and from one to five heteroatoms selected from the group consisting of nitrogen, oxygen, and sulfur, preferably a 4- to 8-membered ring with one or more heteroatoms, more preferably a 5- or 6-membered ring with one or more heteroatoms. For the purposes of this invention, the heterocycle may be a monocyclic, bicyclic or tricyclic ring system, which may include fused ring systems; and the nitrogen, carbon or sulfur atoms in the heterocyclyl radical may be optionally oxidised; the nitrogen atom may be optionally quaternized; and the heterocyclyl radical may be partially or fully saturated or aromatic. Examples of such heterocycles include, but are not limited to, azepines, benzimidazole, benzothiazole, furan, isothiazole, imidazole, indole, piperidine, piperazine, purine, quinoline, thiadiazole, tetrahydrofuran, coumarine, morpholine; pyrrole, pyrazole, oxazole, isoxazole, triazole, imidazole, etc.

"Alkoxy" refers to a radical of the formula —ORa where Ra is an alkyl radical as defined above, e.g., methoxy, ethoxy, propoxy, etc.

"Alkoxycarbonyl" refers to a radical of the formula —C(O)ORa where Ra is an alkyl radical as defined above, e.g., methoxycarbonyl, ethoxycarbonyl, propoxycarbonyl, etc.

"Alkylthio" refers to a radical of the formula —SRa where Ra is an alkyl radical as defined above, e.g., methylthio, ethylthio, propylthio, etc.

"Amino" refers to a radical of the formula —NH2, —NHRa or —NRaRb, optionally quaternized.

"Halo" or "hal" refers to bromo, chloro, iodo or fluoro.

References herein to substituted groups in the compounds of the present invention refer to the specified moiety that may be substituted at one or more available positions by one or more suitable groups, e.g., halogen such as fluoro, chloro, bromo and iodo; cyano; hydroxyl; nitro; azido; alkanoyl such as a C1-6 alkanoyl group such as acyl and the like; carboxamido; alkyl groups including those groups having 1 to about 12 carbon atoms or from 1 to about 6 carbon atoms and more preferably 1-3 carbon atoms; alkenyl and alkynyl groups including groups having one or more unsaturated linkages and from 2 to about 12 carbon or from 2 to about 6 carbon atoms; alkoxy groups having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulfinyl groups including those moieties having one or more sulfinyl linkages and from 1 to about 12 carbon atoms or from 1 to about 6 carbon atoms; alkylsulfonyl groups including those moieties having one or more sulfonyl linkages and from 1 to about 12 carbon atoms or from 1 to about 6 carbon atoms; aminoalkyl groups such as groups having one or more N atoms and from 1 to about 12 carbon atoms or from 1 to about 6 carbon atoms; carbocylic aryl having 6 or more carbons, particularly phenyl or naphthyl and aralkyl such as benzyl. Unless otherwise indicated, an optionally substituted group may have a substituent at each substitutable position of the group, and each substitution is independent of the other.

Particular individual compounds of the invention include the compounds 1-86 in the examples, either as salts or as free bases.

In an embodiment the 2,2a,4,5-tetrahydro-1H-3-aza-acenaphthylen in the compounds of formula I above is not substituted, $R^1$ to $R^7$ are all H. Good activity results are obtained with such compounds.

In another embodiment $R^2$ and $R^3$ are alkoxy, preferably methoxy and the rest of the substitutents of the 2,2a,4,5-tetrahydro-1H-3-aza-acenaphthylen ($R^1$ and $R^4$ to $R^7$) are H.

In another embodiment $R^2$ is alkoxy, preferably methoxy and the rest of the substitutents of the 2,2a,4,5-tetrahydro-1H-3-aza-acenaphthylen ($R^1$ and $R^3$ to $R^7$) are H.

In another embodiment the group W linked to the sulfonamide is aromatic, such as substituted or unsubstituted aryl, substituted or unsubstituted heterocyclyl, preferably substituted or unsubstituted phenyl. Good results were obtained when W is alkyl, alkoxy and/or halo substituted phenyl. In particular halo substituted phenyl, having one or more halo substituents being the same or different are preferred.

In another embodiment it is important that n is 3 or 4.

The above embodiments and preferences for W, $R^1$ to $R^7$ and n can be combined to give further preferred compounds.

Representative compounds of the above embodiments which are preferred are 4-Chloro-2,5-dimethyl-N-[4-(2,2a,4-5-tetrahydro-1H-3-aza-acenaphthylen-3-yl)-butyl]-ben-zenesulfonamide hydrochloride, 2,5-Dichloro-N-[3-(2,2a,4-5-tetrahydro-1H-3-aza-acenaphthylen-3-yl)-propyl]-benzenesulfonamide hydrochloride, 2,5-Dichloro-N-[3-(7,8-dimethoxy-2,2a,4-5-tetrahydro-1H-3-aza-acenaphthylen-3-yl)-propyl]-benzene sulfona-mide hydrochloride, 2-Chloro-N-[3-(7,8-dimethoxy-2,2a,4-5-tetrahydro-1H-3-aza-acenaphthylen-3-yl)-propyl]-4,5-difluoro-benzene sulfonamide hydrochloride.

The compounds of the present invention represented by the above described formula (I) may include enantiomers depending on the presence of chiral centres or isomers depending on the presence of multiple bonds (e.g. Z, E). The single isomers, enantiomers or diastereoisomers and mixtures thereof fall within the scope of the present invention.

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by a $^{13}C$- or 14C-enriched carbon or $^{15}N$-enriched nitrogen are within the scope of this invention.

The term "pharmaceutically acceptable salts, solvates, prodrugs" refers to any pharmaceutically acceptable salt, ester, solvate, or any other compound which, upon administration to the recipient is capable of providing (directly or indirectly) a compound as described herein. However, it will be appreciated that non-pharmaceutically acceptable salts also fall within the scope of the invention since those may be useful in the preparation of pharmaceutically acceptable salts. The preparation of salts, prodrugs and derivatives can be carried out by methods known in the art.

For instance, pharmaceutically acceptable salts of compounds provided herein are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate. Examples of the alkali addition salts include inorganic salts such as, for example, sodium, potassium, calcium, ammonium, magnesium, aluminium and lithium salts, and organic alkali salts such as, for example, ethylenediamine, ethanolamine, N,N-dialkylenethanolamine, triethanolamine, glucamine and basic aminoacids salts.

Particularly favored derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Any compound that is a prodrug of a compound of formula (I) is within the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides.

The compounds of the invention may be in crystalline form either as free compounds or as solvates and it is intended that both forms are within the scope of the present invention. Methods of solvation are generally known within the art. Suitable solvates are pharmaceutically acceptable solvates. In a particular embodiment the solvate is a hydrate.

The compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts, solvates or prodrugs.

Compounds of Formula (I) can be prepared by the coupling of a compound of Formula (II):

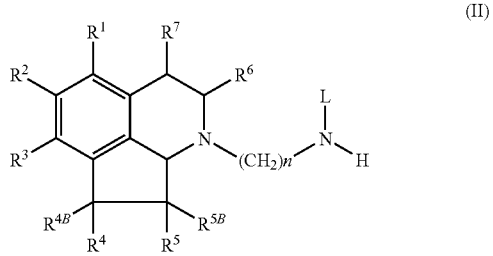

(II)

in which $R^1$-$R^7$, L and n are as defined in Formula (I), with a compound of Formula (III):

(III)

in which W is as defined in Formula (I) and X is an halogen, typically Cl.

The reaction of compounds of formulas (II) and (III) is preferably carried out in an aprotic solvent, but not limited to, such as dichloromethane in the presence of an organic base, such as diisopropylethylamine or triethylamine.

Compounds of Formula (III) are commercially available or can be prepared by conventional methods.

Compounds of Formula (II) can be prepared from compounds of Formula (IV) or compounds of Formula (V) using the reactions described below.

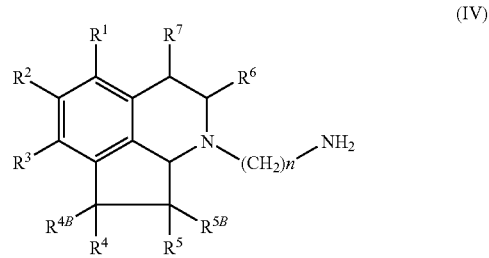

(IV)

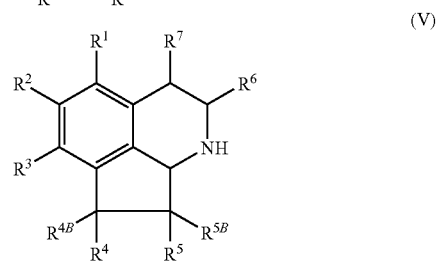

(V)

The preparation of these two compounds are later described in the text.

Compounds of Formula (II) from Compounds of Formula (IV):

If L=CH$_2$L' compounds of Formula (IV) can be acylated with a carboxylic acid derivative (L'COX), where X is a good leaving group, such as halogen (Cl or Br) or with an anhydride of L' (L'COOCOL'), followed by a reduction (Scheme 1). The acylation can be done in the presence of an appropriate base, such as pyridine and a solvent such as dichloromethane, or using a bifasic system consisting of a mixture of dichloromethane/water using an inorganic base such as NaHCO$_3$. The reduction of the carbonyl group can be afforded by an hydride, such as LiAlH$_4$.

Scheme 1

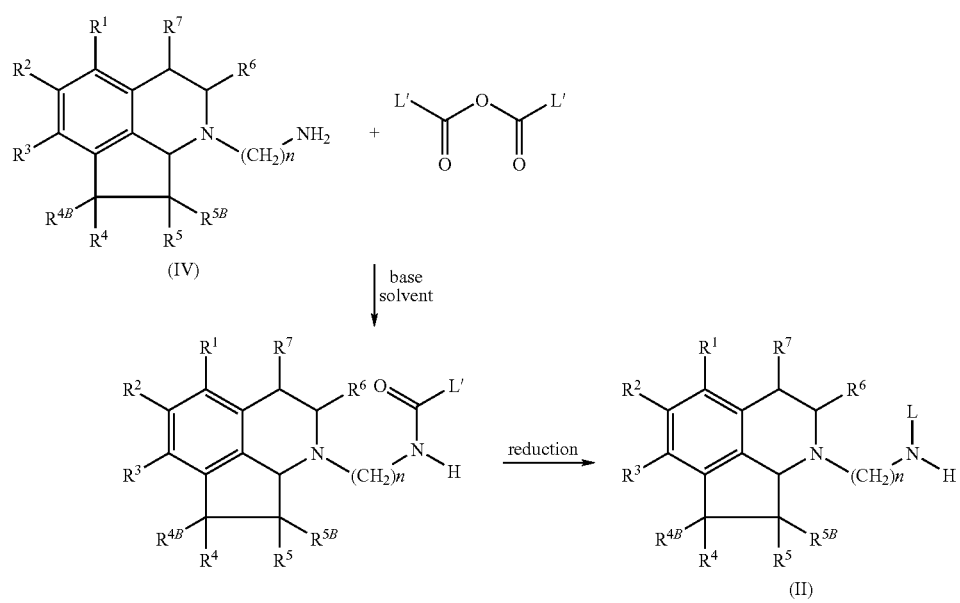

If L is alkyl or cycloalkyl, compounds of Formula (II) can also be obtained by an alkylation of IV with a variety of alkyl compounds containing a good leaving group such as Br, I, aryl or alkylsulfonate . . . in the presence of an appropriate base and solvent, as shown in Scheme 2. Useful bases include, but are not limited to, metal carbonates or bicarbonates (NaHCO$_3$, K$_2$CO$_3$ . . . ) Typical solvents include polar aprotic liquids such as DMF or THF.

Scheme 2

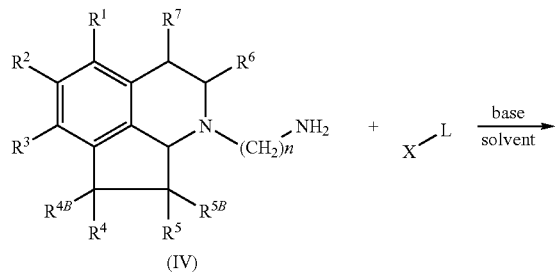

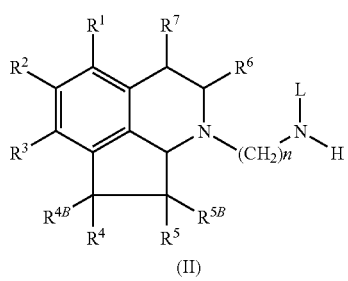

(II)

If L is aryl or heteroaryl, the N-arylation can be achieved by a cross coupling reaction with X-L, where X is a halogen or alkyl or aryl sulfonate, using a catalytic system consisting of a metal, such as Pd, Cu and a ligand such as phosphine, in the presence of a dry solvent such as toluene or dioxane and an appropriate base such as Cs$_2$CO$_3$ or tBuOK (Scheme 3).

Scheme 3

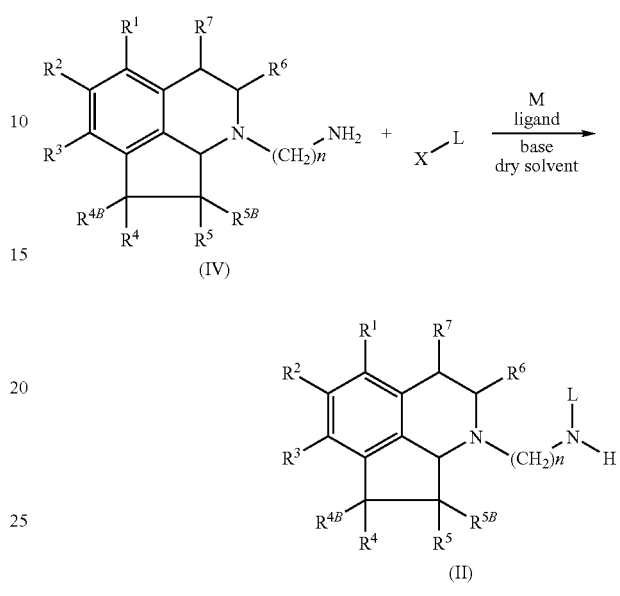

Compounds of Formula (II) from Compounds of Formula (V):

The synthesis can be done in a sequential way by treatment of the amine of Formula (V) with a dialkylating agent (VI) in the presence of a base in an appropriate solvent, followed by the alkylation of a primary amine substituted with L (VII). This sequence is illustrated in Scheme 4.

Scheme 4

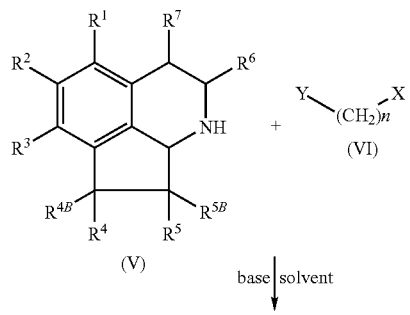

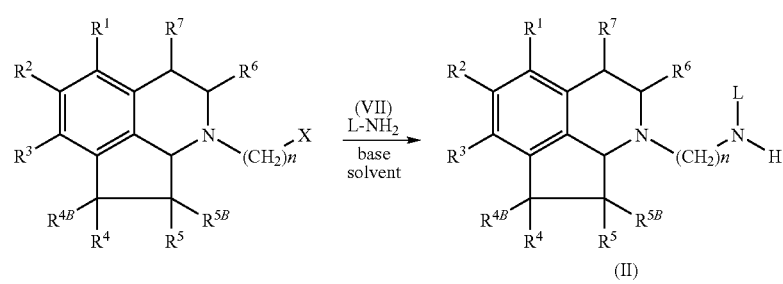

Examples of useful alkylating agents are those where Y is a good to excellent leaving group, such as Br, I, aryl or alkylsulfonate . . . and X is a good leaving group, such as Br or Cl. Useful bases include, but are not limited to, metal carbonates such as $K_2CO_3$ or $Cs_2CO_3$, metal hydroxides, hindered alkoxides or tertiary organic amines. Typical solvents include polar aprotic liquids such as DMF or THF, or protic liquids such as alcohols. The rate of the second alkylation may be enhaced, particularly when X is Cl, by the addition of a catalytic amount of a iodide salt, such as NaI or KI.

Compounds of Formula (II) can also be prepared from compounds of Formula (V) by an alkylation with a secondary amine substituted with L and with an alkyl chain containing a good leaving group, such as Br, I, alkyl or aryl sulfonate . . . (VIII) In Scheme 5, the amino group of VIII should be protected to avoid side reactions. Some examples of protecting groups include a variety of carbamates, such as BOC; Fmoc . . . a variety of amides, such as acetamides, and alkyl and aryl amine derivatives, such as N-benzyl, N-allyl . . . . Deprotection of these protecting groups may be performed using conventional methods. The alkylation can be done using the same solvents and bases described above. The protection of the amino group of compounds of Formula (VIII) can be avoided if its reactivity is much lower than the reactivity of the amino group of compounds of Formula (V).

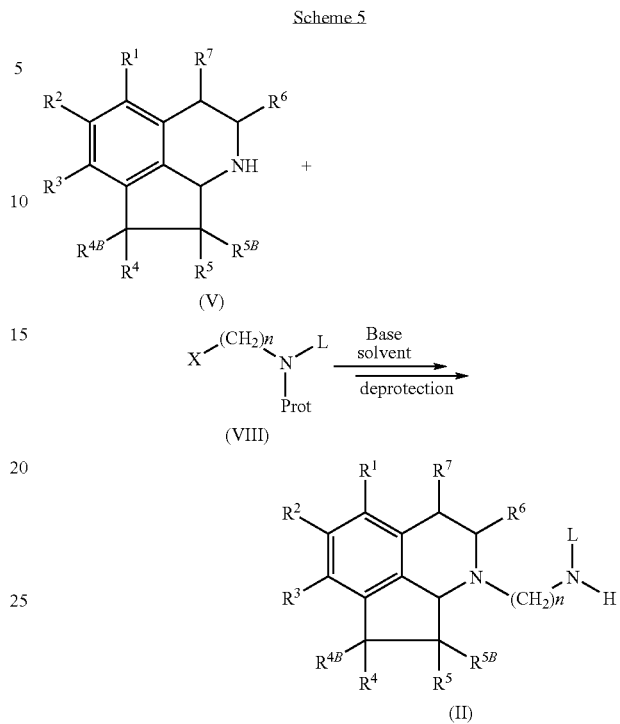

Another way to some compounds of Formula (II) from compounds of Formula (V) (Scheme 6) can be by an alkylation with haloalkylamides (IX) in an appropriate solvent and base, the same as are cited in Schemes above. Intermediate (X) may be reduced in the presence of a hydride, such as $LiAlH_4$ or borane.

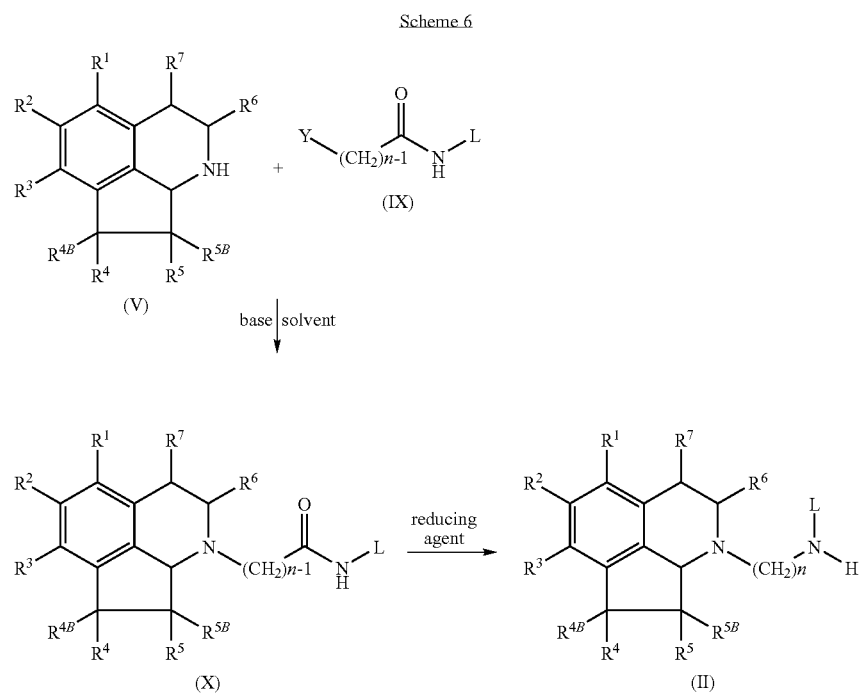

An alternative way to compounds of Formula (II) from compounds of Formula (V) (Scheme 7) can be achieved using compounds of Formula (XI) and a condensating agent such as N,N-dicyclohexylcarbodiimide (DCC) or 1-ethyl-3-(3-dimethylaminopropyl)carbodiimide (EDC), carbonyldiimadazole, O-Benzotriazole-N,N,N',N'-tetramethyl-uronium-hexafluoro-phosphate (HBTU) or benzotriazol-N-oxotris (dimethylamino) phosphonium hexafluorophosphate (BOP)), among others, in the presence of an aprotic solvent, such as DMF and an organic base, such as triethylamine. Then, a reduction of the two amide groups of compounds of Formula (XII) in a dry solvent, such as tetrahydrofurane, in the presence of an hydride, such as LiAlH$_4$, can lead to compounds of Formula (II), as shown in Scheme 7.

Preparation of Compounds of Formula (V):

Amines of Formula (V) can be prepared by methods and techniques described below. References for cited described methods are incorporated.

A variety of substituted compounds of Formula (V) shown in Scheme 8 can be achieved from compounds of Formula (Va). Total reduction from this ketone by hydrogenation at high pressure in the presence of concentrated acid, such as HCl, or with hydrazine in a Wolff-Kischner reaction, or using Clemensen-type conditions with HCl and Zn can lead to compounds of Formula (Vb). Partial reduction with an hydride, such as NaBH$_4$, can lead to the alcohol of Formula (Ve), which can also be reduced to compounds of Formula (Vb) by a hydrogenation.

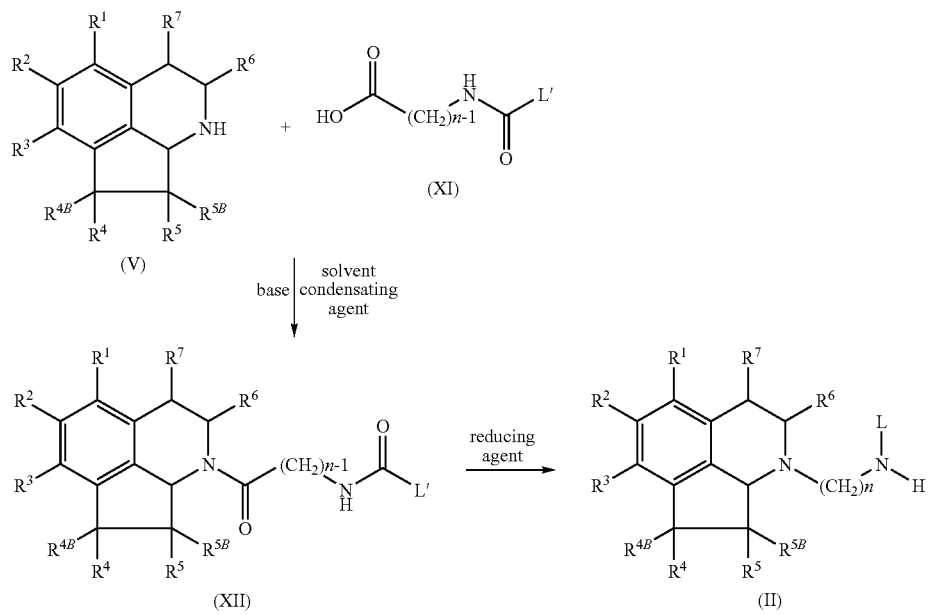

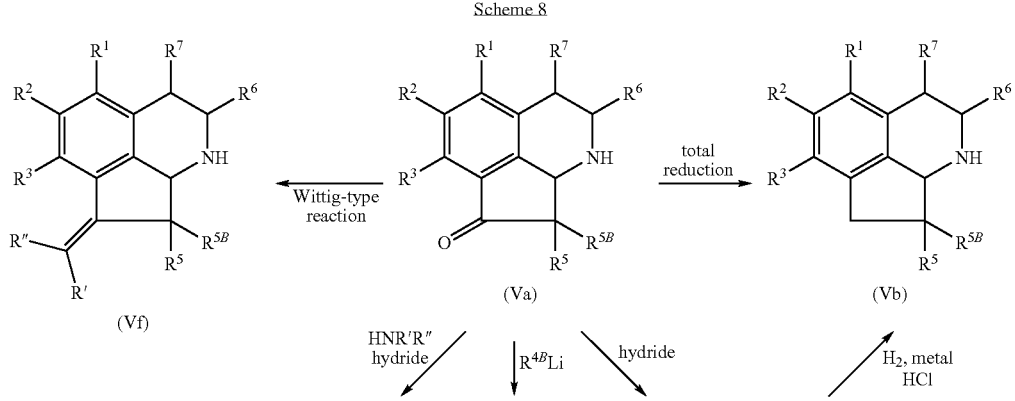

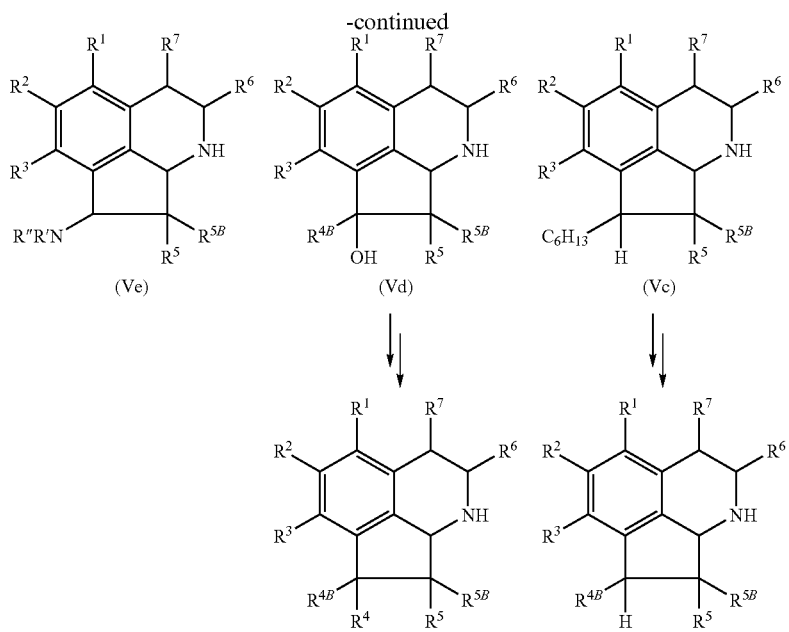

The introduction of substitution in the ketone (Va) can be done, among others, by a nucleophilic attack with organometallics, such as lithium reagents ($R^{4B}Li$) to yield the compound (Vd), by reductive amination with an amine (RR'NH) and an hydride such as $NaBH(OAc)_3$ to yield (Ve), or by C—C bond formation with phosphonium ylides o phosphonates in a Wittig-type reaction to yield (Vf).... Some of these methods need the protection of the amino group. The protecting groups used can be those which have been described above. All these compounds can be further derivatized using conventional organic reactions.

Compounds of Formula (Va) can be obtained from a β-aminoacid (XIII) by a Friedel-Crafts acylation (Scheme 9). This acylation can be carried out in the presence of a strong acid, such as polyphosphoric acid, methanesulfonic acid . . . or a Lewis acid, such as $AlCl_3$ . . . at high temperature (100-200° C.). Unsubstituted compound of Formula (Va), 2a,3,4,5-Tetrahydro-2H-3-aza-acenaphthylen-1-one, can be prepared from 2-(1,2,3,4-tetrahydroisoquinolin-1-yl)acetic acid, according the methods described in *J. Org. Chem.* 1987, 52, 616-622 and in *Heterocycles,* 1989, 29(12), 2399-2402. Nevertheless, these methods have been improved by the use of microwave radiation instead of conventional heating (see examples later in the text).

Scheme 9

The β-aminoacid (XIII) can be prepared by a sequential or one-pot synthesis starting from substituted phenylethyl amines.

The multi-step synthesis (Scheme 10) can start with a Pictet-Spengler reaction with formaldehyde to yield a substituted tetrahydroisoquinoline (XIV). The oxidation of the benzylic position α to the N can be achieved by a bromination with NBS followed by an elimination in the presence of a base to yield a substituted dihydroisoquinoline (XV). An aldolic reaction with a α,α-disubstituted acetic acid with $R^5$ and $R^{5B}$ can lead to the β-aminoacid (XIII).

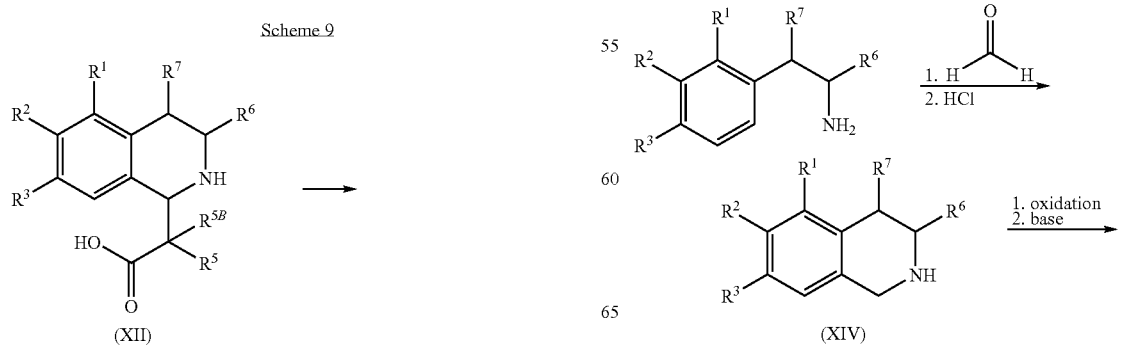

Scheme 10

-continued

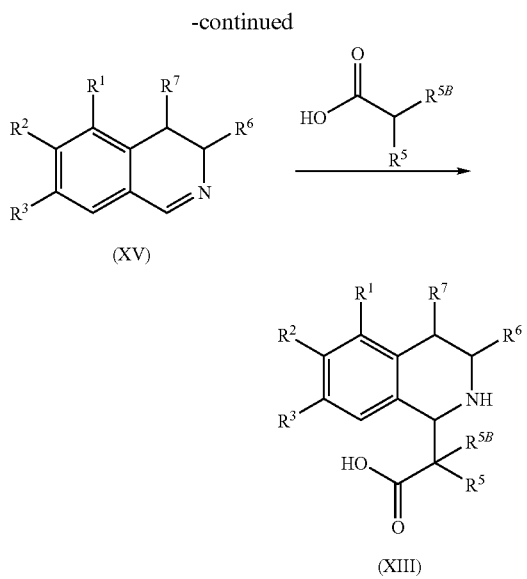

(XV)

(XIII)

This reaction is especially favoured when a substituted malonic acid is used, because of a decarboxylation process at high temperature (100-150° C.), but then, only one substitution ($R^5$ or $R^{5B}$) can be introduced. The other substitution has to be necessarily a H, as shown in Scheme 11.

Scheme 11

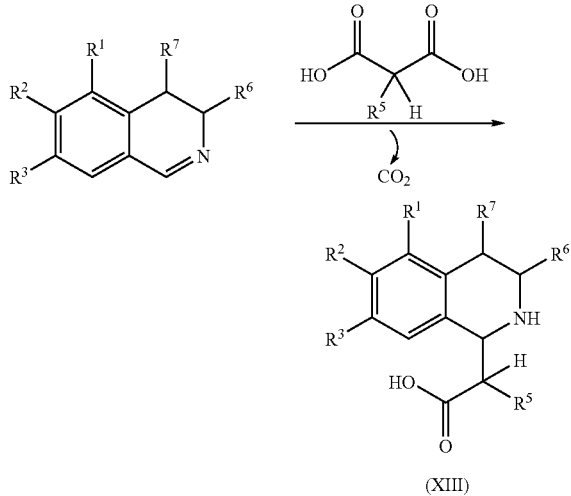

(XIII)

The one-pot synthesis can also be performed by a Pictet-Spengler reaction, in the presence of 3-oxopropanoic acid derivative α,α-disubstituted with $R^5$ and $R^{5B}$ (Scheme 12)

Scheme 12

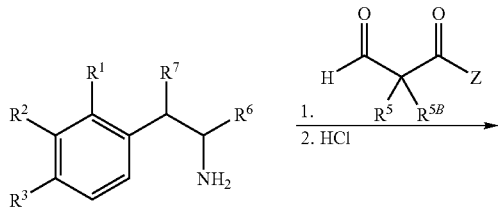

-continued

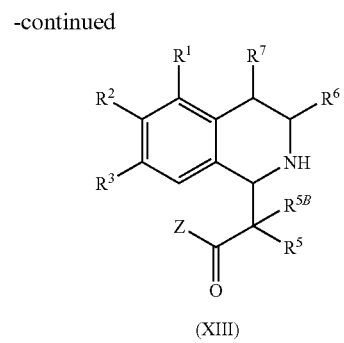

(XIII)

Other possible way to compounds of Formula (V) is starting from a phenylethyl amine and a malonic acid derivative α,α-disubstituted with $R^5$ and $R^{5B}$ by a Bischler-Napieralsky reaction, as shown in Scheme 13a). The selective reduction of the imine bond of compound of Formula (XVI) can lead to the desired compounds of Formula (V), which could be further derivatized. This method also allows to achieve chiral compounds of Formula (V) if the reduction step consists of an asymmetric hydrogenation catalyzed by complexes formed by a transition methal, such as rhodium or ruthenium and a chiral ligand, such as phosphine or phosphane. Methodologies for an asymmetric hydrogenation of ketones or imines are described in *J. Am. Chem. Soc.* 1996, 118, 4916, *J. Am. Chem. Soc.* 1996, 118, 5142, *J. Org. Chem.* 1998, 63, 6084. Another suitable method for the obtention of a chiral compound of Formula (Va) or (V) is shown in Scheme 13 b). Starting from a isoquinoline, a enantioselective acyl-Mannich-type reaction is catalyzed by a chiral thiourea derivative to give a chiral dihydroisoquinoline, which can lead to compound of Formula (Va) by a hydrolisis, deprotection of the nitrogen atom (*Angew. Chem. Int. Ed.* 2005, 44, 6700-6704) and a cyclization by a Friedel-Crafts acylation (Scheme 9).

Scheme 13 a)

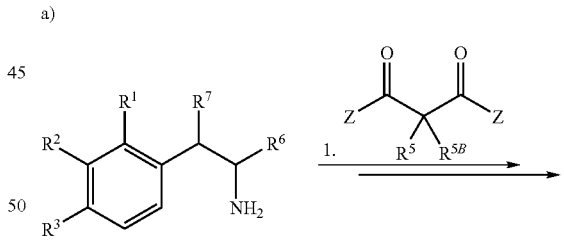

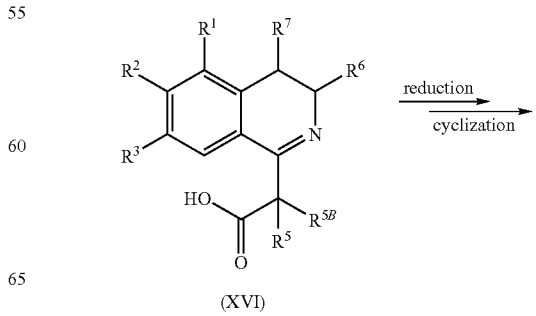

(XVI)

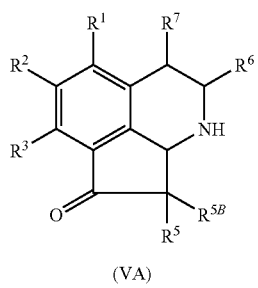

(VA)

b)

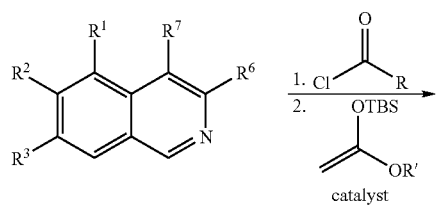

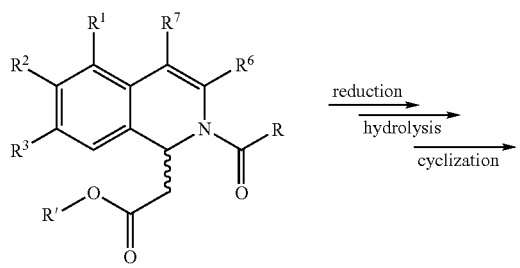

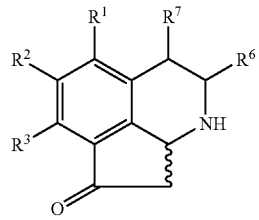

(Va)

Where convenient, a variety of substituted compounds of Formula (V) can be achieved from compounds of Formula (XVII) by the multi-step synthesis shown in Scheme 14. Compounds of Formula (XVII) are commercially available or prepared by conventional methods.

Scheme 14

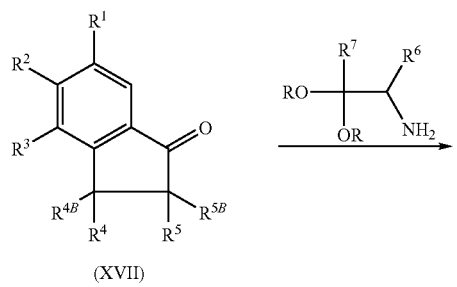

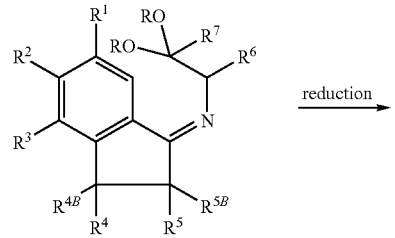

(XVIII)

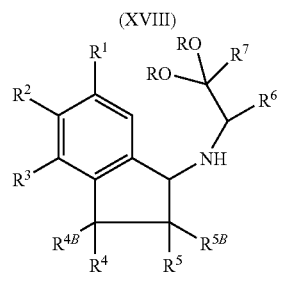

(XIX)

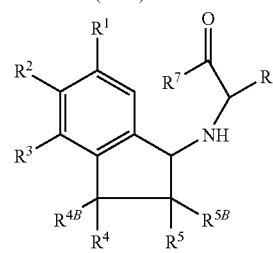

(XX)

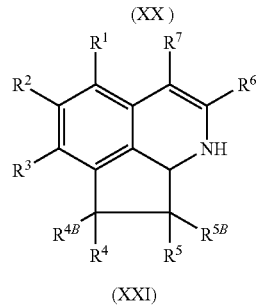

(XXI)

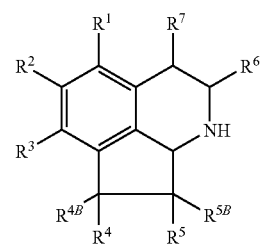

(V)

The sequence can start with a reductive amination of compounds of Formula (XVII) with an aminoketal substituted with $R^6$ and $R^7$. The use of ketals instead of unprotected aldehydes or ketones is convenient to avoid side-reactions, such as polymerization of the bifunctionalyzed amines. The reduction of the resulting imine (XVIII) by hydrogenation lead to the aminoketal (XIX). The hydrolysis of the ketal in acid media, such as hydrochloric acid lead to a keto compound (XX) or directly to the dihydroisoquinoline (XXI), which can be reduced by a hydrogenation to yield the desired compounds of Formula (V). The preparation by this method of the unsubstituted compound of Formula (Va), 1,2,2a,3,4,5-Hexahydro-2H-3-aza-acenaphthylen, and the compound substituted with $R^2=R^3=OCH_3$, 7,8-Dimethoxy-1,2,2a,3,4,5-hexahydro-3-aza-acenaphthylene, is described in *J. Org. Chem.* 1971, 36(1), 111-117.

Preparation of Compounds of Formula (IV):

Compounds of Formula (IV) can be prepared from compounds of Formula (V) using the reactions and techniques described below.

The reactions are performed in a solvent appropriate to the reagents and materials employed and suitable for the transformations. The functionality present on the molecule should be consistent with the transformations proposed. This will sometimes require a selection of a particular process scheme over another in order to obtain the desired compound of the invention. Preferred methods included, but are not limited to, those described below.

Compounds of Formula (IV) can be prepared by alkylation as shown in Scheme 15.

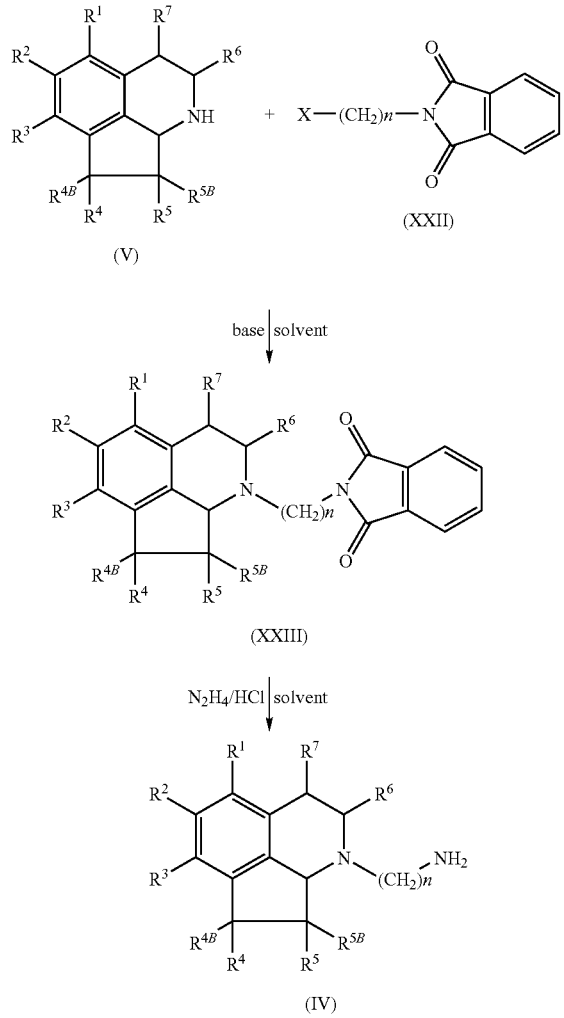

alkoxides or tertiary organic amines. Typical solvents include polar aprotic liquids such as DMF or THF, or protic liquids such as alcohols. In a second step, the hydrazinolysis of the alkylated compound (XXIII) using hydrazine in a polar protic solvent, such as ethanol, and hydrochloric acid gives the desired compound of Formula (IV).

A similar route to compounds of Formula (IV) is illustrated in Scheme 16.

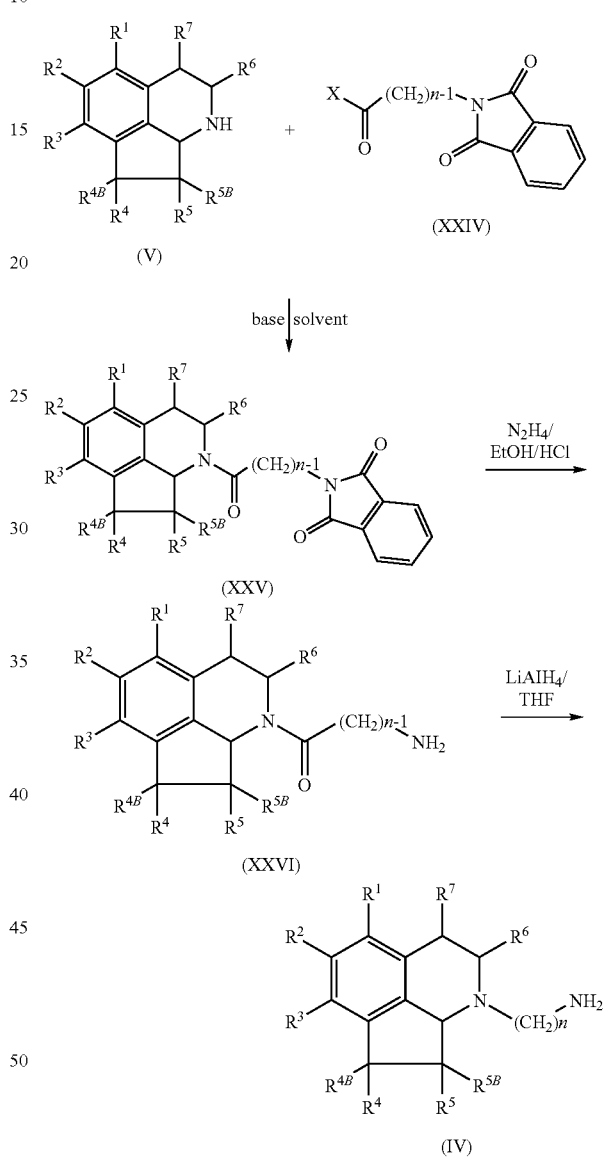

The acylation of compounds of Formula (V) with carboxyalkylphtalimides derivatives (XXIV), instead of the alkylation with N-(n-haloalkyl)phtalimides (XXII), may be convenient in some cases. When X is a Cl or Br, or other good leaving group, the base used for acylation can be a tertiary organic amine such as triethylamine or N,N-diisopropylethylamine and the hydrazinolysis can be performed as cited in Scheme 15. When X is an OH, a coupling reagent must be used for the activation of carboxy group. Many coupling reagents are known in the literature to form amide bonds from carboxylic acids and amines, including DCC, EDC, HBTU, TBTU, BOP, PyBOP . . . . Appropriate bases for such cou- In the first step, the amine of Formula (V) is allowed to react with a commercially available N-(n-haloalkyl)phtalimide (XXII) in the presence of an appropriate base and solvent. Useful bases include, but are not limited to, metal carbonates such as $K_2CO_3$ or $CS_2CO_3$, metal hydroxides, hindered pling reactions include tertiary amines such as N,N-diisopropylethylamine, triethylamine . . . . The activated species are usually not isolated, but are allowed to react in situ with the amine partner (V).

After the hydrazinolysis of phtalimide (XXV), the reduction of the amide intermediate (XXVI) may be performed with a reducing agent, such as borane or lithium aluminum hydride in appropriate solvent, typically THF.

A similar method to compounds of Formula (IV) is illustrated in Scheme 17.

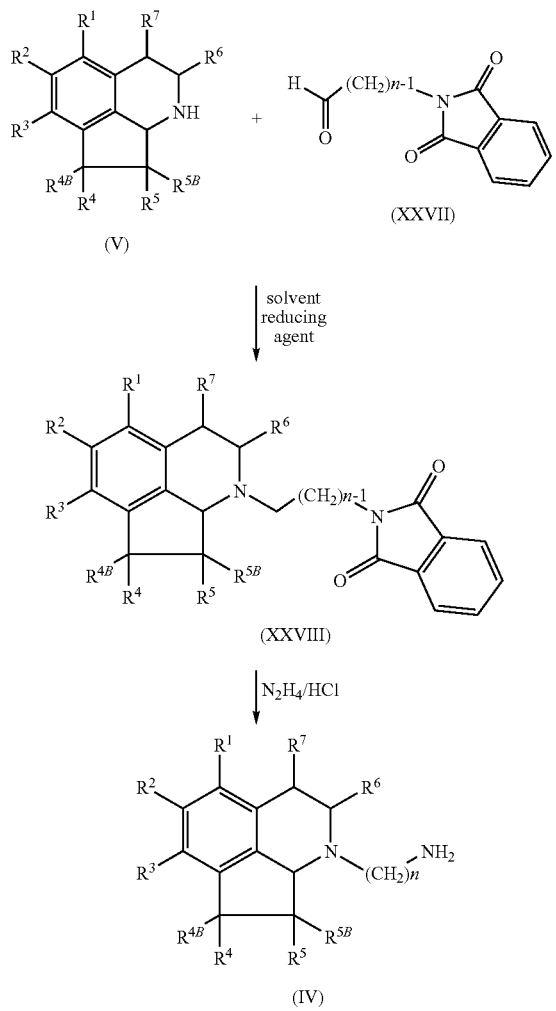

A reductive amination with phtalimidoalkylaldehydes (XXVII), following by hydrazinolysis may also be performed. Condensation of the amine (V) with aldehydes (XXVII) can be performed in the presence of a hydride, such as sodium triacethoxyborohydride NaBH(OAc)$_3$ or sodium cyanoborhydride (NaBH$_4$CN). Phtalimide intermediate (XXVIII) is treated as is described in Schemes 15 and 16 in order to obtain the desired compound of Formula (IV).

In all these Schemes, other protecting groups for the nitrogen atom, instead of the phtalimide, may be used. Some examples include other cyclic imide derivatives, such as maleimides or succinimides, a variety of carbamates, such as BOC (an example is illustrated in Scheme 18); Fmoc . . . a variety of amides, such as acetamides, and alkyl and aryl amine derivatives, such as N-benzyl, N-allyl . . . . Deprotection of these protecting groups may be performed using conventional methods.

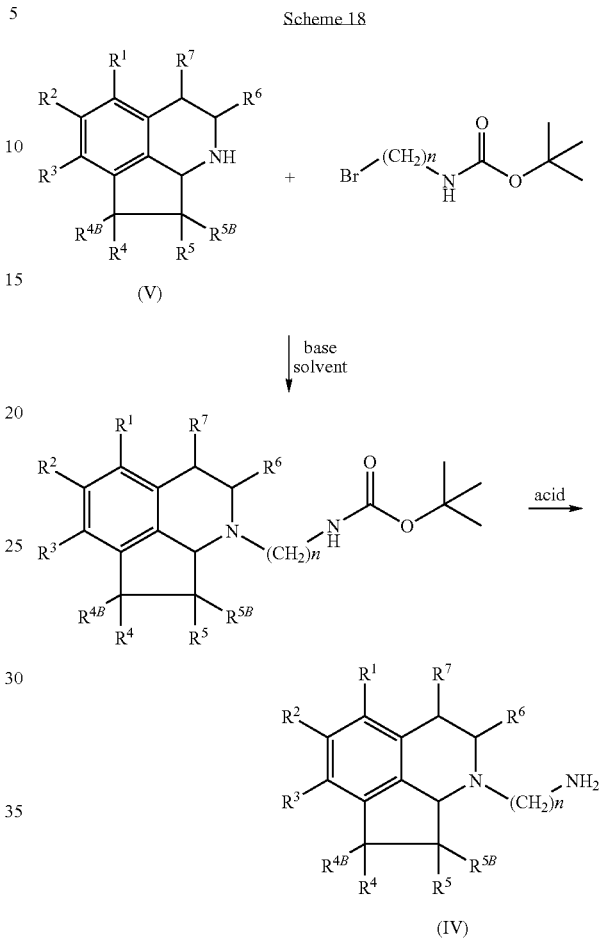

This Scheme is especially useful in the case where R$_4$ and R$_{4B}$ together form a keto group, in order to avoid the reduction steps needed in the Schemes above, for the deprotection of the amino group of the alkylic chain, which can alter the ketone.

Where convenient, compounds of Formula (IV) can be prepared as shown in Scheme 19.

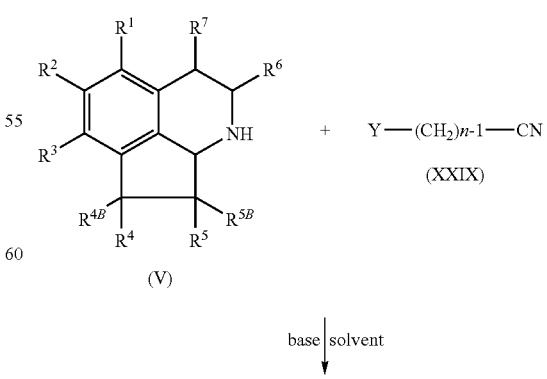

-continued

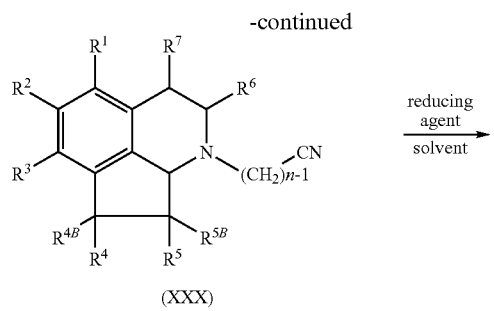

(XXX)

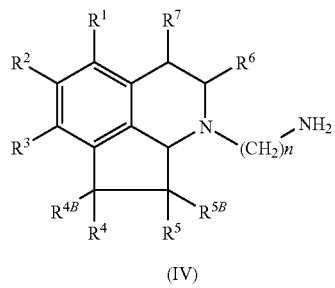

(IV)

The alkylation of compounds of Formula (V) with commercially available haloalkylnitriles (XXIX) can be performed in the presence of a variety of bases and solvents cited in schemes above. For the reduction of the cyano group of (XXX), common reducing agents, such as LiAlH$_4$ in THF, can be used. A catalytic hydrogenation with Pd/C in ethanol is also possible.

In some cases, an acylation with carboxynitriles to form an amide is preferred instead of the alkylation with the corresponding halonitriles (Scheme 20).

Scheme 20

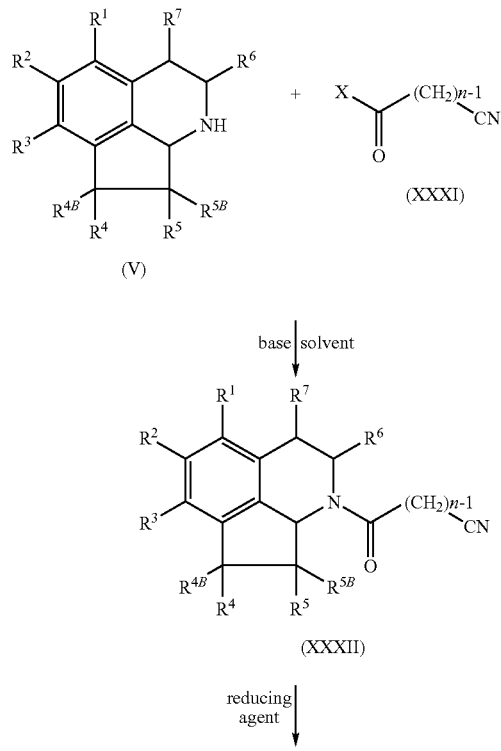

-continued

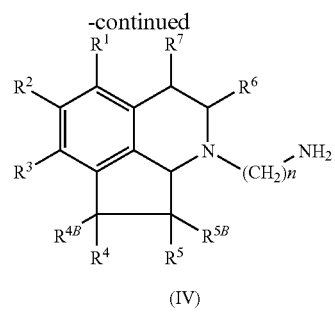

(IV)

The acylation of compounds of Formula (V) with compounds of Formula (XXXI), where X is a good leaving group, such as Cl or Br, is carried out in the presence of an appropriate base and solvent, which were described in schemes above. The reduction of cyano and keto group of XXXII can be performed simultaneously in the presence of an excess of a reducing agent such as LiAlH$_4$ or borane. When X is OH, a coupling reagent must also be used for the activation of carboxy group. The coupling reagents used are the same as are cited in Scheme 16.

Scheme 20 is also possible when X is an H. Reductive amination is carried out by a condensation of amine of Formula (V) with aldehyde of Formula XXXI in appropriate base and solvent, to form an imine or enamine intermediate, followed by a reduction with a reducing agent, such an hydride.

Preparation of Compounds of Formula (I) from Compounds of Formula (Ib):

When L=aryl or heteroaryl, compounds of Formula (I) can also be obtained by the coupling of compounds of Formula (Ib), with an aryl or heteroaryl containing an electrowithdrawing and good leaving group (Y), such as a halogen or alkyl or aryl sulfonate, using catalytic cross coupling reaction conditions (Scheme 21). Compounds of Formula (Ib) can be synthesized by the coupling of compounds of Formula (IV) with compounds of Formula (III) following the methods described for the preparation of compounds of Formula (I) when L=H.

Scheme 21

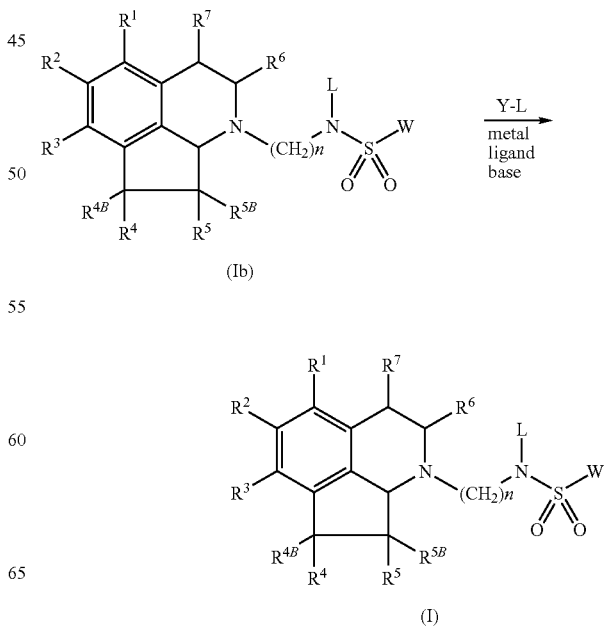

In some cases, although L=alkyl or cycloalkyl, compounds of Formula (I) can also be conveniently prepared from compounds of Formula (Ib), by an alkylation of the nitrogen of the sulfonamide group, using an strong base, such as NaH in an aprotic and dry solvent, such as THF, in the presence of an alkylating agent, such as ethyl iodide as shown in Scheme 22.

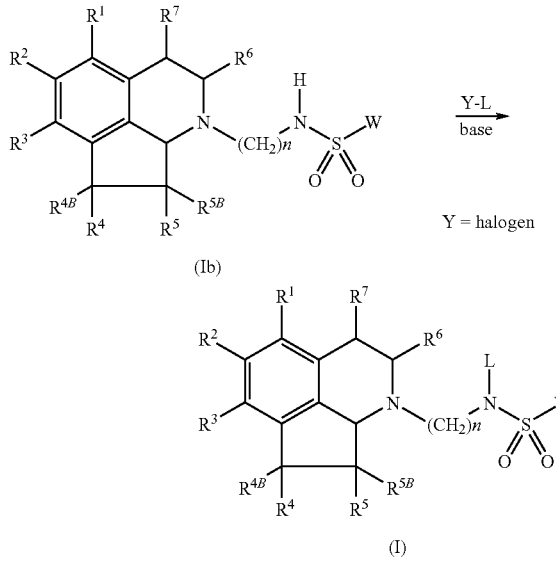

This Scheme is especially useful in the case where $R_4$ and $R_{4B}$ together form a keto group, in order to avoid the reduction steps needed in other Schemes, which can alter the ketone. When $R^4$ and $R^{4B}$ together form a keto group, Scheme 2 (see above) is also a suitable method to obtain compounds of Formula (II) from compounds of Formula (IV).

Nevertheless, if $R_4$ and $R_{4B}$ together form a keto group, compounds of Formula (I) can also be prepared using all the methods described in the Schemes above, but using protecting groups for the keto group, in order to avoid the reduction of this group in the steps where other reduction is required. Some examples include acyclic ketals, such as dimethyl or diisopropyl, or cyclic ketals, such as 1,3-dioxanes or 1,3-dioxolanes. Protection and deprotection steps may be performed using conventional methods.

The following Descriptions and Examples illustrate the preparation of compounds of the invention.

The obtained reaction products may, if desired, be purified by conventional methods, such as crystallisation, chromatography and trituration. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

One preferred pharmaceutically acceptable form is the crystalline form, including such form in pharmaceutical composition. In the case of salts and solvates the additional ionic and solvent moieties must also be non-toxic. The compounds of the invention may present different polymorphic forms, it is intended that the invention encompasses all such forms.

Another aspect of this invention relates to a method of treating or preventing an 5-$HT_7$ mediated disease which method comprises administering to a patient in need of such a treatment a therapeutically effective amount of a compound of formula (I) or a pharmaceutical composition thereof. Among the 5-$HT_7$ mediated diseases that can be treated are diseases caused by failures in central and peripheral serotonin-controlling functions, such as pain, sleep disorder, shift worker syndrome, jet lag, depression, seasonal affective disorder, migraine, anxiethy, psychosis, schizophrenia, cognition and memory disorders, neuronal degeneration resulting from ischemic events, cardiovascular diseases such as hypertension, irritable bowel syndrome, inflammatory bowel disease, spastic colon or urinary incontinence.

The present invention further provides pharmaceutical compositions comprising a compound of this invention, or a pharmaceutically acceptable salt, derivative, prodrug or stereoisomers thereof together with a pharmaceutically acceptable carrier, adjuvant, or vehicle, for administration to a patient.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrups or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

The following examples are given only as further illustration of the invention, they should not be taken as a definition of the limits of the invention.

EXAMPLES

Compounds of general Formula (I) were prepared by means of conventional organic chemistry methods known to those skilled in the art and some examples are described below. The preparation of some of the intermediates of general formulas (V), (IV) and (II) is also shown below.

Example A

This is an example of a compound of general Formula (Va). 2a,3,4,5-Tetrahydro-2H-3-aza-acenaphthylen-1-one can be prepared from 2-(1,2,3,4-tetrahydroisoquinolin-1-yl)acetic acid, according the methods described in *J. Org. Chem.* 1987, 52, 616-622 and in *Heterocycles,* 1989, 29(12), 2399-2402, which are hereby incorporated by reference and form part of the disclosure. Nevertheless, these methods were improved by the use of microwave radiation instead of conventional heating.

2a,3,4,5-Tetrahydro-2H-3-aza-acenaphthylen-1-one

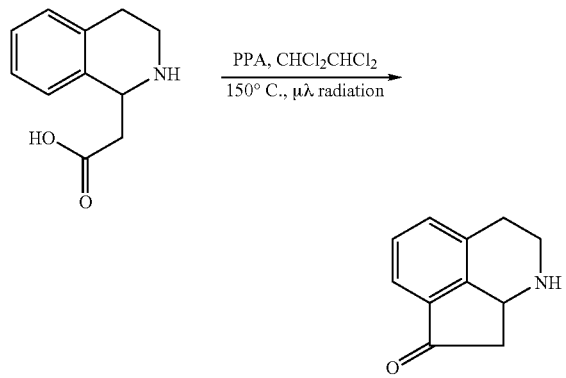

Polyphosphoric acid (30 g) was added to a suspension of 2-(1,2,3,4-tetrahydroisoquinolin-1-yl)acetic acid (2 g) in 1,1,2,2-tetrachloroethane (6 ml) and the mixture was allowed to react in a CEM Explorer microwave apparatus working at 150° C. and at 150 W for 45 min. The crude was poured to a mixture of ice/water to destroy the PPA, made alkaline with 25% ammonia and extracted with dichloromethane. The combined organic layers were dried with $Na_2SO_4$ and evaporated in vacuo to afford a brown solid (1.7 g, 94% yield), which was purified by silicagel chromatography using a gradient of dichloromethane/methanol to afford a light brown solid identified as 2a,3,4,5-Tetrahydro-2H-3-aza-acenaphthylen-1-one.

$^1$H NMR (300 MHz, CHLOROFORM-D) δ ppm 2.47 (dd, J=17.13, 6.30 Hz, 1H) 2.55 (s, 1H) 2.90 (m, 2H) 2.99 (dd, J=17.06, 6.66 Hz, 1H) 3.25 (ddd, J=12.70, 9.11, 7.32 Hz, 1H) 3.44 (ddd, J=12.74, 5.56, 3.22 Hz, 1H) 4.21 (t, J=6.37 Hz, 1H) 7.29 (m, 2H) 7.45 (t, J=4.25 Hz, 1H) MS (APCI (M+H)$^+$): 174

Example B

This is an example of a compound of general Formula (V). 1,2,2a,3,4,5-Hexahydro-3-aza-acenaphthylen can be prepared according the method described in *J. Med. Chem.* 1988, 31(2), 433-443, or according the method described in *Heterocycles,* 1989, 29(12), 2399-2402, which are hereby incorporated by reference and form part of the disclosure. These methods have been slightly modified in order to obtain a better yield in only one step.

1,2,2a,3,4,5-Hexahydro-3-aza-acenaphthylene hydrochloride

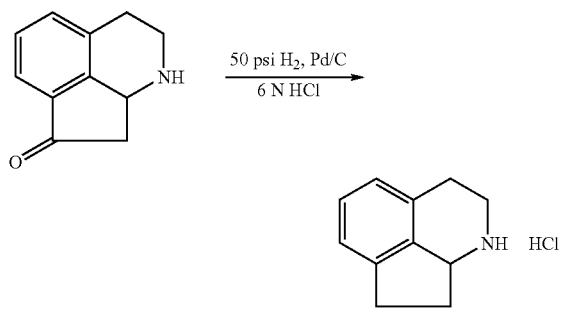

A solution of 2a,3,4,5-Tetrahydro-2H-3-aza-acenaphthylen-1-one (2 g, 11.5 mmol) in 6 N hydrochloric acid (150 ml) containing 10% Pd/C was hydrogenated at 50 psi of $H_2$ for 24 h. The catalyst was filtered, the solution was basified with 20% NaOH and extracted with dichloromethane (3×150 ml). The organic layers were dried over $Na_2SO_4$ and concentrated to dryness to afford a colorless oil (1.6 g, 85% yield) identified as 1,2,2a,3,4,5-Hexahydro-3-aza-acenaphthylene. The addition of 2.8 N hydrochloric acid in ethanol yielded the hydrochloride as a white solid, which was collected by filtration.

$^1$H NMR (300 MHz, CHLOROFORM-D) δ ppm 1.69 (qd, J=11.23, 8.30 Hz, 1H) 2.46 (m, 1H) 2.75 (m, 3H) 2.88 (m, 1H) 3.16 (ddd, J=12.82, 10.50, 6.23 Hz, 1H) 3.43 (ddd, J=12.82, 6.23, 1.95 Hz, 1H) 4.06 (dd, J=10.62, 6.47 Hz, 1H) 6.93 (d, J=7.32 Hz, 1H) 7.04 (m, 1H) 7.12 (t, J=7.32 Hz, 1H) MS (APCI (M+H)$^+$): 160

Example C

This is an example of a compound of general Formula (IV) from a compound of general formula (V).

2,3-Dihydro-benzofuran-5-sulfonic acid [3-(2,2a,4,5-tetrahydro-1H-3-aza-acenaphthy-len-3-yl)-propyl]-amide hydrochloride a) 2-[3-(2,2a,4,5-Tetrahydro-1H-3-aza-acenaphthylen-3-yl)-propyl]-isoindole1,3-dione

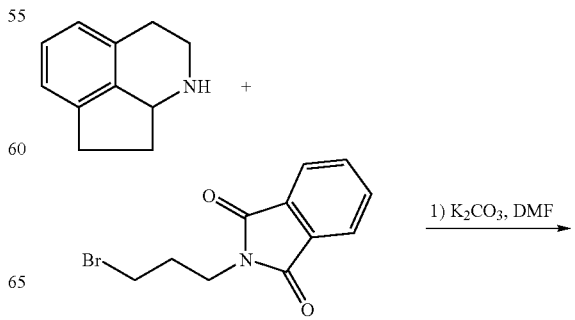

-continued

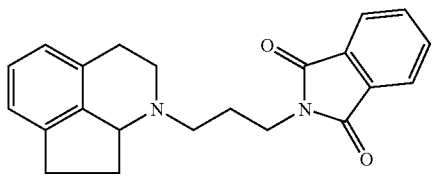

A mixture of 1,2,2a,3,4,5-Hexahydro-3-aza-acenaphthylene (1.1 g, 6.92 mmol), N-(4-Bromopropyl)phtalimide (1.97 g, 7.33 mmol) and potassium carbonate (2.8 g, 20.76 mol) in dry N,N'-dimethylformamide (10 mL), was stirred overnight at room temperature. The mixture was vacuum concentrated and the residue was dissolved in water (10 mL), extracted with ethyl acetate (3×10 mL) and washed with water. The organic layer was dried and evaporated to give the product (2.20 g, 92% yield).

$^1$H NMR (300 MHz, DMSO-D6) δ ppm 1.48-1.64 (m, 1H) 1.85 (dt, J=13.66, 6.87 Hz, 2H) 2.15-2.27 (m, 2H) 2.27-2.38 (m, 1H) 2.63-2.78 (m, 4H) 3.15 (dd, J=11.72, 5.86 Hz, 1H) 3.21-3.29 (m, 1H) 3.54-3.71 (m, 2H) 6.83 (d, J=6.88 Hz, 1H) 6.94-7.08 (m, 2H) 7.75-7.87 (m, J=11.57, 9.19, 4.21, 2.42 Hz, 4H) MS (APCI (M+H)$^+$): 347

) 3-(2,2a,4,5-Tetrahydro-1H-3-aza-acenaphthylen-3-yl)-propylamine dihydrochloride

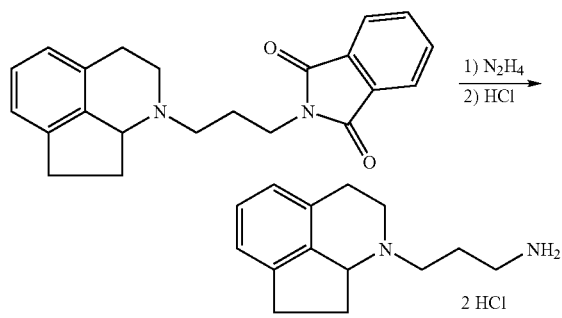

A solution of 2-[3-(2,2a,4,5-Tetrahydro-1H-3-aza-acenaphthylen-3-yl)-propyl]-isoindole1,3-dione (2 g, 5.78 mmol) and hydrazine hydrate (2.9 g, 57.8 mol) in ethanol (60 mL) was refluxed for 1 h. The reaction mixture was cooled down and treated with an additional amount of ethanol (30 mL) and concentrated HCl (7 mL). Then the reaction mixture was refluxed for 4 h and left overnight in a refrigerator. The precipitate was filtered off, and the solvent was evaporated. The residue was redissolved in water (15 ml) and made alkaline with 25% ammonia. Then, was extracted with CH$_2$Cl$_2$ (3×120 mL), the organic layer was dried over Na$_2$SO$_4$, and evaporated to dryness. The crude was dissolved in ethylacetate. A 2.8 M solution of hydrogen chloride in ethanol was then added. The precipitate formed was collected by filtration to give the desired product (0.80 g, 64% yield) as a beige solid.

$^1$H NMR (300 MHz, DMSO-D6) δ ppm 2.14 (m, 3H) 2.63 (m, 1H) 2.90 (m, 4H) 3.15 (m, 3H) 3.48 (m, 2H) 3.80 (m, 1H) 4.59 (m, 1H) 7.07 (d, J=7.47 Hz, 1H) 7.16 (d, J=7.47 Hz, 1H) 7.25 (t, J=7.47 Hz, 1H) 8.22 (s, 2H) 10.99 (br, 1H) MS (APCI (M+H)$^+$): 217

Example D

This is an example of a compound of general Formula (II) from a compound of general formula (V).

[3-(2,2a,4,5-Tetrahydro-1H-3-aza-acenaphthylen-3-yl)-propyl]-m-tolyl-amine a) 3-(3-Chloro-propyl)-1,2,2a,3,4,5-hexahydro-3-aza-acenaphthylene

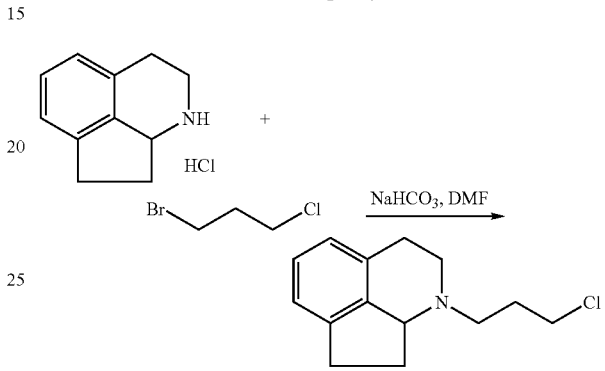

To a solution of 1,2,2a,3,4,5-Hexahydro-3-aza-acenaphthylene hydrochloride (500 mg, 2.56 mmol) in dry N,N'-dimethylformamide (5 ml) was added NaHCO$_3$ (620 mg, 12.8 mmol) and 1-bromo-3-chloropropyl (420 mg, 2.68 mmol) and the mixture was stirred overnight at room temperature. The mixture was vacuum concentrated and the residue was dissolved in water (15 mL), extracted with ethyl acetate (3×15 mL) and washed with water. The organic layer was dried and evaporated to give the desired product (250 mg, 70% yield).

MS (APCI (M+H)$^+$): 236 b) [3-(2,2a,4,5-Tetrahydro-1H-3-aza-acenaphthylen-3-yl)-propyl]-m-tolyl-amine dihydrochloride

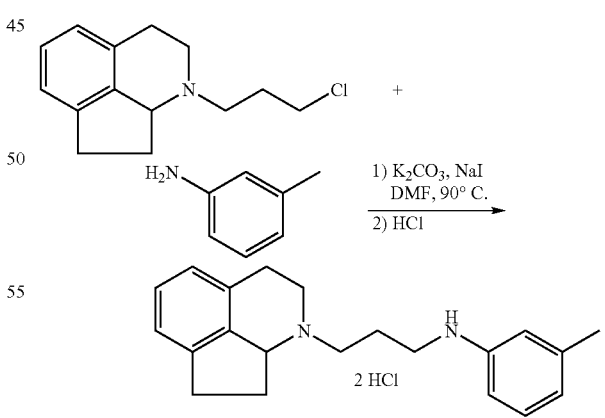

To a solution of m-tolylamine (21.7 mg, 0.20 mmol) in dry DMF (2 ml) was added K$_2$CO$_3$ (31 mg, 0.22 mmol), NaI (33 mg, 0.22 mmol) and 3-(3-Chloro-propyl)-1,2,2a,3,4,5-hexahydro-3-aza-acenaphthylene (50 mg, 0.21 mmol) and the mixture was stirred overnight at 90° C. The mixture was vacuum concentrated and the residue was dissolved in water (5 mL), extracted with ethyl acetate (3×5 mL) and washed with water. The organic layer was dried and evaporated. The residue was dissolved in ethyl acetate (1 ml) and 2.8 N hydrochloric acid was added. A light brown solid precipitate, which was collected by filtration to give the desired product (40 mg, 66% yield).

$^1$H NMR (300 MHz, DMSO-D6) δ ppm 2.09 (m, 3H) 2.25 (s, 3H) 2.61 (m, 1H) 2.88 (d, J=7.82 Hz, 2H) 3.10 (m, 2H) 3.24 (m, 2H) 3.41 (m, 2H) 3.82 (m, 2H) 4.60 (m, 1H) 6.82 (m, 2H) 7.07 (d, J=7.42 Hz, 1H) 7.16 (m, 2H) 7.25 (m, 2H) MS (APCI (M+H)$^+$): 307

Example E

This is an example of a compound of general Formula (II) from a compound of general Formula (IV).

Ethyl-[3-(2,2a,4,5-tetrahydro-1H-3-aza-acenaphthylen-3-yl)-propyl]-amine a) N-[3-(2,2a,4,5-Tetrahydro-1H-3-aza-acenaphthylen-3-yl)-propyl]-acetamide 3-(2,2a,4,5-Tetrahydro-1H-3'-aza-acenaphthylen-3-yl)-propylamine (516 mg, 2.39 mmol) was dissolved in a vigorously stirred mixture of CH$_2$Cl$_2$ (2.7 ml) and NaHCO$_3$ (sat. solution, 2.7 ml). After the addition of acetic anhydride (348.9 mg, 3.42 mmol), stirring was applied for 90 min at room temperature. Then, the layers were separated. Water (6 ml) was added to the bicarbonate layer and was extracted with CH$_2$Cl$_2$ (3×6 ml). The combined organic layers were dried with Na$_2$SO$_4$, filtered and evaporated to dryness to afford as slightly brown solid identified as the acetylated compound (535 mg, 87% yield).

$^1$H NMR (300 MHz, DMSO-D6) δ ppm 1.58 (m, 3H) 1.75 (s, 3H) 2.17 (m, 2H) 2.36 (m, 1H) 2.71 (m, 5H) 3.04 (ddd, J=12.60, 6.96, 3.00 Hz, 2H) 3.16 (m, 1H) 3.28 (m, 1H) 6.87 (d, J=7.18 Hz, 1H) 7.02 (m, 2H) 7.80 (br, 1H) MS (APCI (M+H)$^+$): 259 b) Ethyl-[3-(2,2a,4,5-tetrahydro-1H-3-aza-acenaphthylen-3-yl)-propyl]-amine dihydro-chloride N-[3-(2,2a,4,5-Tetrahydro-1H-3-aza-acenaphthylen-3-yl)-propyl]-acetamide (478 mg, 1.85 mmol) was dissolved in THF (dry, 13 ml) and added dropwise to a suspension of 1 M LiALH$_4$ (3.7 ml, 3.7 mmol) in dry THF under argon atmosphere. The mixture was refluxed overnight. Water and 1 N NaOH was added to the crude. The salts formed were filtered over Celite and the filtrate was extracted with CH$_2$Cl$_2$, dried with Na$_2$SO$_4$ and evaporated in vacuo. The colorless oil obtained (427 mg, 94% yield) was purified by silicagel chromatography using a gradient of CH$_2$Cl$_2$/methanol. A 2,8 M solution of hydrogen chloride in ethanol was then added. The precipitate formed was collected by filtration to give the desired product (436 mg, 75% yield) as a white solid.

$^1$H NMR (300 MHz, DMSO-D6) δ ppm 1.21 (t, J=7.18 Hz, 3H) 2.14 (m, 3H) 2.65 (m, 1H) 2.91 (m, 6H) 3.17 (m, 3H) 3.48 (m, 2H) 3.84 (d, J=11.28 Hz, 1H) 4.60 (m, 1H) 7.08 (d, J=7.32 Hz, 1H) 7.17 (d, J=7.18 Hz, 1H) 7.26 (m, 1H) 9.17 (br, 2H) 10.88 (br, 1H) MS (APCI (M+H)$^+$): 245

Example F

This is an example of a compound of general Formula (II) from a compound of general Formula (V).

Ethyl-[3-(7,8-Dimethoxy-2,2a,4,5-tetrahydro-1H-3-aza-acenaphthylen-3-yl)-propyl]-amine a) N-[3-(7,8-Dimethoxy-2,2a,4,5-tetrahydro-1H-3-aza-acenaphthylen-3-yl)-3-oxo-propyl]-acetamide A suspension of N-(3-Dimethylaminopropyl)-N'-ethylcarbodiimide hydrochloride (1.14 g, 5.93 mmol) and triethylamine (4 ml) in N,N-Dimethylformamide (30 ml) is stirred at room temperature. Then, 1-Hydroxybenzotriazole (0.698 g, 4.56 mmol), 7,8-Dimethoxy-1,2,2a,3,4,5-hexahydro-3-aza-acenaphthylene hydrochloride (1.0 g, 4.56 mmol) and N-acetil-3-aminopropanoic acid (0.657 g, 5.0 mmol) were added and the crude is stirred at room temperature for 15 h. Then, water (60 ml) and CH$_2$Cl$_2$ (60 ml) are added to the crude. Organic layer is separated and the aqueous one is extracted with CH$_2$Cl$_2$ (2×60 ml). All the organic layers were collected and washed with 0.1 N HCl (3×60 ml), with NaHCO$_3$ (3×60 ml) sat and with water (3×40 ml). After drying with Na$_2$SO$_4$, filtration and vacuum concentration, a beige oil is obtained (1.32 g, 87% yield). The oil is crystallized in ethyl acetate to give a beige solid (1.0 g, 66% yield).

$^1$H NMR (300 MHz, DMSO-D6) δ ppm 1.76 (s, 3H) 2.46 (m, 2H) 2.60 (m, 4H) 2.81 (m, 3H) 3.25 (m, 2H) 3.70 (s, 3H) 3.72 (s, 3H) 3.95 (m, 1H) 4.68 (m, 1H) 6.72 (s, 1H) 7.88 (t, J=5.35 Hz, 1H) MS (APCI (M+H)$^+$): 333 b)-Ethyl-[3-(7,8-Dimethoxy-2,2a,4,5-tetrahydro-1H-3-aza-acenaphthylen-3-yl)-propyl]-amine dihydrochloride

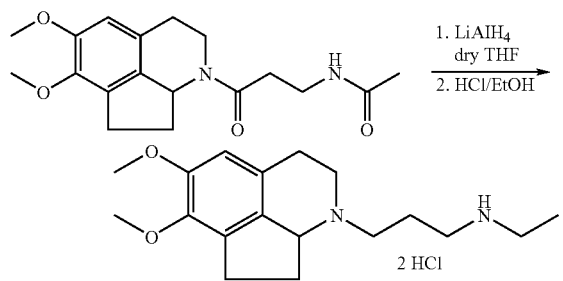

N-[3-(7,8-Dimethoxy-2,2a,4,5-tetrahydro-1H-3-aza-acenaphthylen-3-yl)-3-oxo-propyl]aceta-mide (370 mg, 1.1 mmol) was dissolved in THF (dry, 10 ml) and added dropwise to a suspension of 1 M LiALH$_4$ (11 ml, 11 mmol) in dry THF under argon atmosphere. The mixture was refluxed for 4 hours. A solution of saturated sodium tartrate (20 ml) was added to the crude and the mixture is stirred for 1 hour. Then, extracted with ethyl acetate (3×20 ml), dried over Na$_2$SO$_4$, filtered and evaporated to dryness to afford an oil (304 mg, 90% yield), which is precipitate with a solution of 2.8 N HCl/EtOH and ethyl acetate, to afford Ethyl-[3-(7,8-Dimethoxy-2,2a,4,5-tetrahydro-1H-3-aza-acenaphthylen-3-yl)-propyl]-amine dihydrochloride (333 mg, 80% yield).

$^1$H NMR (300 MHz, DMSO-D6) δ ppm 1.20 (t, J=7.10 Hz, 3H) 2.13 (m, 3H) 2.61 (m, 1H) 2.93 (m, 8H) 3.17 (m, 2H) 3.48 (m, 1H) 3.73 (s, 3H) 3.75 (s, 3H) 3.79 (m, 1H) 4.50 (q, J=9.08 Hz, 1H) 6.77 (s, 1H) 9.12 (br, 2H) 10.72 (br, 1H) MS (APCI (M+H)$^+$): 305

Example G

This is an example of a compound of general Formula (IV) from a compound of general Formula (Va).

3-(3-Amino-propyl)-2a,3,4,5-tetrahydro-2H-3-aza-acenaphthylen-1-one a) [4-(7,8-Dimethoxy-1-oxo-2,2a,4,5-tetrahydro-1H-3-aza-acenaphthylen-3-yl)-butyl]-carbamic acid tert-butyl ester

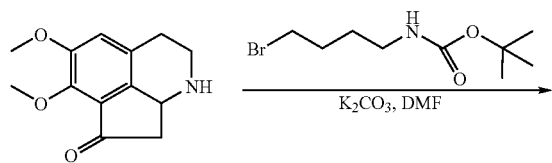

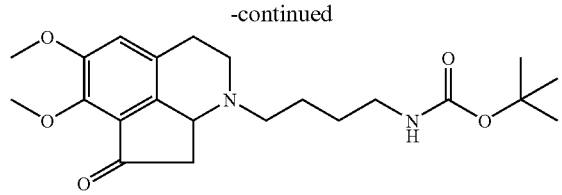

Over a suspension of 7,8-Dimethoxy-2a,3,4,5-tetrahydro-2H-3-aza-acenaphthylen-1-one (0.950 g, 4.1 mmol), K$_2$CO$_3$ (1.89 g, 13.6 mmol) and NaI (0.061 g, 0.4 mmol) in DMF (20 ml) is slowed added (4-Bromo-butyl)-carbamic acid tert-butyl ester (1.09 g, 4.32 mmol) and the mixture is stirred overnight. Then, water (40 ml) and ethyl acetate (40 ml) are added and the layers are separated. The aqueous phase is extracted with ethyl acetate (2×40 ml). The organic layers are collected and washed with water (3×40 ml). After drying with Na$_2$SO$_4$, filtration and vacuum concentration, a brown oil is obtained, which is purified by silicagel chromatography using a gradient of CH$_2$Cl$_2$/methanol (from 100% to 98% CH$_2$Cl$_2$) to obtain a brown solid (0.730 g, 45% yield)

$^1$H NMR (300 MHz, DMSO-D6) δ ppm 1.41 (s, 9H) 1.58 (m, 3H) 2.41 (m, 2H) 2.68 (m, 2H) 2.92 (m, 3H) 3.14 (m, 2H) 3.38 (m, 1H) 3.58 (m, 1H) 3.85 (s, 3H) 4.04 (s, 3H) 4.84 (m, 1H) 6.92 (s, 1H) MS (APCI (M+H)$^+$): 405 b) 3-(4-Amino-butyl)-7,8-dimethoxy-2a,3,4,5-tetrahydro-2H-3-aza-acenaphthylen-1-one dihydrochloride

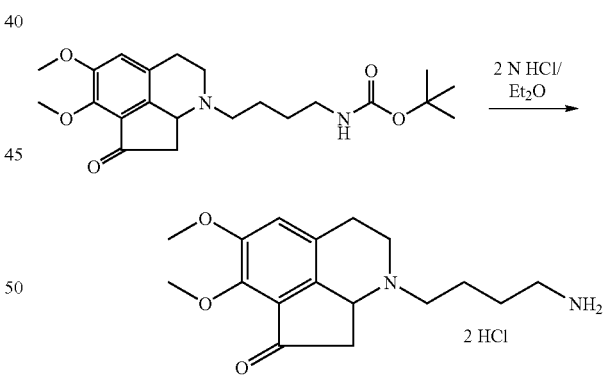

[4-(7,8-Dimethoxy-1-oxo-2,2a,4,5-tetrahydro-1H-3-aza-acenaphthylen-3-yl)-butyl]-carbamic acid tert-butyl ester (498 mg, 1.22 mmol) is dissolved in a mixture of CH$_2$Cl$_2$ (10 ml) and ethanol (2 ml) and a solution of 2 N HCl in Et$_2$O is added (6 ml, 12 mmol). A brown precipitate appears, which is collected by filtration (367 mg, 80% yield).

$^1$H NMR (300 MHz, DMSO-D6) δ ppm 1.61 (m, 2H) 1.87 (m, 2H) 2.81 (m, 2H) 3.10 (m, 6H) 3.48 (m, 2H) 3.82 (s, 3H) 3.87 (s, 3H) 4.75 (m, 1H) 7.30 (s, 1H) 8.02 (s, 3H) 11.33 (br, 1H) MS (APCI (M+H)$^+$): 305

Example H 2,3-Dihydro-benzofuran-5-sulfonic acid [3-(2,2a,4,5-tetrahydro-1H-3-aza-acenaphthylen-3-yl)-propyl]-amide hydrochloride (28)

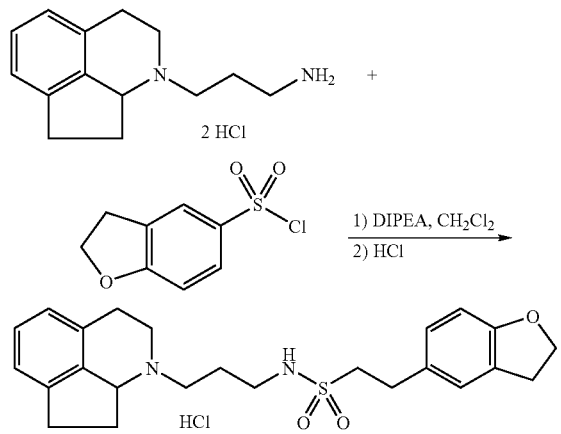

2,3-Dihydro-benzofuran-5-sulfonyl chloride (24.05 mg, 0.11 mmol) was added to a solution of 3-(2,2a,4,5-Tetrahydro-1H-3-aza-acenaphthylen-3-yl)-propylamine dihydrochloride (28.92 mg, 0.1, mmol) and N,N'-diisopropylethylamine (51.7 mg, 0.4 mmol) in CH$_2$Cl$_2$ (10 mL) and the mixture was stirred overnight at room temperature. The resulting solution was washed with water (3×10 mL), dried over Na$_2$SO$_4$ and evaporated to dryness. The free base was dissolved in ethyl acetate (1 ml). A 2.8 M solution of hydrogen chloride in ethanol (0.10 mL) was then added. The product was crystallized and collected by filtration, and vacuum dried to give a white solid (33 mg, 77%).

$^1$H NMR (300 MHz, DMSO-D6) δ ppm 1.92 (m, 4H) 2.56 (m, 1H) 2.83 (m, 4H) 3.09 (m, 3H) 3.24 (m, 2H) 3.39 (m, 1H) 3.77 (d, J=11.13 Hz, 1H) 4.62 (m, 3H) 6.93 (d, J=8.49 Hz, 1H) 7.08 (d, J=7.47 Hz, 1H) 7.17 (m, 1H) 7.26 (t, J=7.47 Hz, 1H) 7.60 (m, 3H) 10.27 (br, 1H) MS (APCI (M+H)$^+$): 399

Example I

N-[3-(2,2a,4,5-Tetrahydro-1H-3-aza-acenaphthylen-3-yl)-propyl]-N-m-tolyl-benzene-sulfonamide hydrochloride (97)

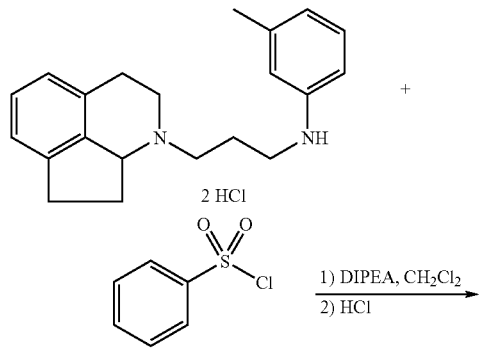

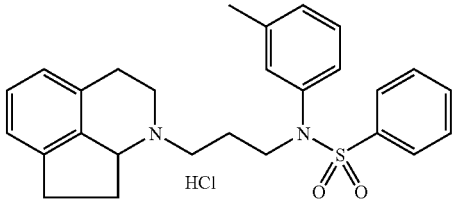

Benzenesulfonyl chloride (48.6 mg, 0.28 mmol) was added to a solution of [3-(2,2a,4,5-Tetrahydro-1H-3-aza-acenaphthylen-3-yl)-propyl]-m-tolyl-amine dihydro-chloride (43.0 mg, 0.11 mmol) and N,N'-diisopropylethylamine (2 ml) in CH$_2$Cl$_2$ (2 mL) and the mixture was stirred overnight at room temperature. The resulting solution was washed with water (3×10 ml), dried over Na$_2$SO$_4$ and evaporated to dryness. The free base was dissolved in ethyl acetate (1 ml). A 2.8 M solution of hydrogen chloride in ethanol (0.10 mL) was then added. The product was crystallized and collected by filtration, and vacuum dried to give a white solid (20.0 mg, 36% yield).

$^1$H NMR (300 MHz, DMSO-D6) δ ppm 1.89 (m, 3H) 2.27 (s, 3H) 2.56 (m, 1H) 2.90 (d, J=7.18 Hz, 2H) 3.08 (m, 2H) 3.20 (td, J=11.94, 5.71 Hz, 1H) 3.41 (m, 2H) 3.69 (m, 2H) 3.76 (m, 1H) 4.62 (q, J=9.52 Hz, 1H) 6.86 (d, J=7.76 Hz, 1H) 6.94 (s, 1H) 7.08 (d, J=7.47 Hz, 1H) 7.17 (m, 2H) 7.27 (t, J=7.62 Hz, 2H) 7.59 (m, 4H) 7.73 (t, J=6.88 Hz, 1H) 10.24 (br, 1H) MS (APCI (M+H)$^+$): 447

Example J

N-Ethyl-4-methyl-N-[3-(2,2a,4,5-tetrahydro-1H-3-aza-acenaphthylen-3-yl)-propyl]-benzenesulfonamide hydrochloride (89)

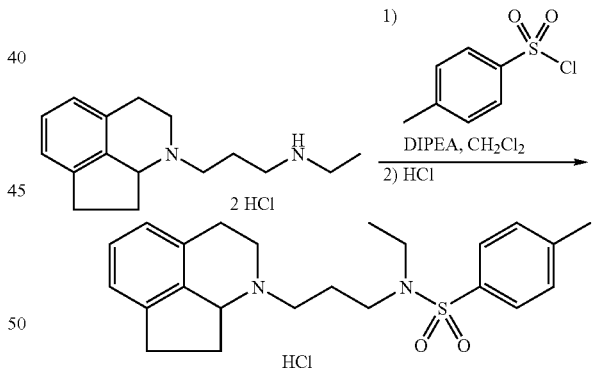

4-Methylbenzenesulfonyl chloride (20.9 mg, 0.11 mmol) was added to a solution of Ethyl-[3-(2,2a,4,5-tetrahydro-1H-3-aza-acenaphthylen-3-yl)-propyl]-amine dihydrochloride (31.7 mg, 0.1 mmol) and N,N'-diisopropylethylamine (64.6 mg, 0.5 mmol) in CH$_2$Cl$_2$ (10 mL) and the mixture was stirred overnight at room temperature. The resulting solution was washed with water (3×10 mL), dried over Na$_2$SO$_4$ and evaporated to dryness. The free base was dissolved in ethyl acetate (1 ml). A 2.8 M solution of hydrogen chloride in ethanol (0.10 mL) was then added. The product was crystallized and collected by filtration, and vacuum dried to give a white solid (18.0 mg, 41%).

$^1$H NMR (300 MHz, DMSO-D6) δ ppm 1.02 (t, J=7.10 Hz, 3H) 2.04 (m, 4H) 2.38 (s, 3H) 2.58 (m, 1H) 2.89 (m, 2H) 3.12

(m, 5H) 3.17 (q, J=7.18 Hz, 2H) 3.42 (m, 1H) 3.85 (d, J=10.99 Hz, 1H) 4.63 (q, J=9.52 Hz, 1H) 7.09 (d, J=7.47 Hz, 1H) 7.17 (m, 1H) 7.27 (t, J=7.47 Hz, 1H) 7.42 (d, J=8.06 Hz, 2H) 7.69 (d, J=8.06 Hz, 2H) 10.36 (br, 1H) MS (APCI (M+H)$^+$): 399

Example K

2-Chloro-N-[3-(7,8-dimethoxy-2,2a,4,5-tetrahydro-1H-3-aza-acenaphthylen-3-yl)-propyl]-N-ethyl-benzenesulfonamide hydrochloride (111)

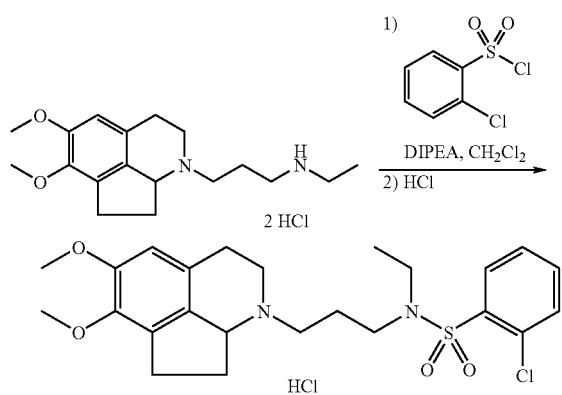

2-Chlorobenzenesulfonyl chloride (246.1 mg, 1.17 mmol) was added to a solution of Ethyl-[3-(7,8-Dimethoxy-2,2a,4,5-tetrahydro-1H-3-aza-acenaphthylen-3-yl)-propyl]-amine dihydro-chloride (400 mg, 1.06 mmol) and N,N'-diisopropylethylamine (1.01 ml, 6.4 mmol) in CH$_2$Cl$_2$ (20 mL) and the mixture was stirred overnight at room temperature. The resulting solution was washed with water (3×20 mL), dried over Na$_2$SO$_4$ and evaporated to dryness. The free base was dissolved in ethyl acetate and A 2.8 M solution of hydrogen chloride in ethanol (0.50 mL) was then added. The product was crystallized and collected by filtration, and vacuum dried to give a white solid (233 mg, 43%).

$^1$H NMR (300 MHz, DMSO-D6) δ ppm 1.00 (t, J=6.96 Hz, 3H) 2.02 (m, 4H) 2.54 (m, 1H) 2.88 (m, 2H) 3.03 (m, 4H) 3.29 (q, J=6.96 Hz, 2H) 3.43 (m, 2H) 3.72 (s, 3H) 3.75 (s, 3H) 3.78 (m, 1H) 4.51 (q, J=9.33 Hz, 1H) 6.78 (s, 1H) 7.56 (m, 1H) 7.68 (qd, J=8.01, 1.46 Hz, 2H) 7.98 (m, 1H) 10.24 (br, 1H). MS (APCI (M+H)$^+$): 479

Example L

2-Chloro-N-[4-(7,8-dimethoxy-1-oxo-2,2a,4,5-tetrahydro-1H-3-aza-acenaphthylen-3-yl)-butyl]-benzenesulfonamide hydrochloride (127)

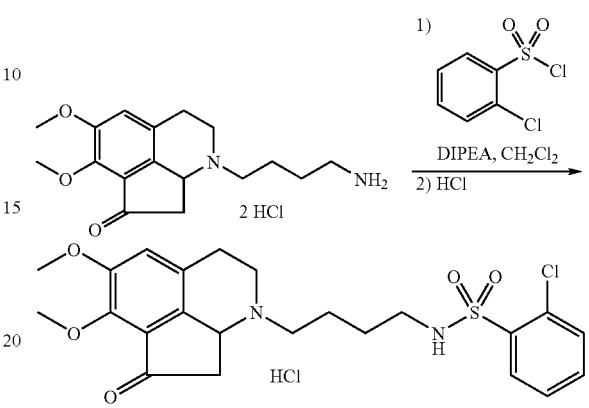

2-Chlorobenzenesulfonyl chloride (92.4 mg, 0.44 mmol) was added to a solution of 3-(4-Amino-butyl)-7,8-dimethoxy-2a,3,4,5-tetrahydro-2H-3-aza-acenaphthylen-1-one dihydro-chloride (150 mg, 0.40 mmol) and NN'-diisopropylethylamine (0.400 ml) in CH$_2$Cl$_2$ (20 mL) and the mixture was stirred overnight at room temperature. The resulting solution was washed with water (3×20 mL), dried over Na$_2$SO$_4$ and evaporated to dryness. The free base was dissolved in ethyl acetate (2 ml) and A 2.8 M solution of hydrogen chloride in ethanol was then added. The product was crystallized and collected by filtration, and vacuum dried to give a pale brown solid (135 mg, 66%).

$^1$H NMR (300 MHz, DMSO-D6) δ ppm 1.47 (m, 2H) 1.73 (m, 2H) 2.86 (m, 2H) 3.10 (m, 6H) 3.45 (m, 2H) 3.82 (s, 3H) 3.87 (s, 3H) 4.72 (m, 1H) 7.30 (s, 1H) 7.54 (m, 1H) 7.66 (m, 2H) 7.98 (m, 2H) 10.80 (br, 1H) MS (APCI (M+H)$^+$): 479

The spectroscopic data for the identification of some of the sulfonamide compounds of the invention having general formula (I), prepared analogously to the methods described in the above examples, are shown in the following table 1:

| N° | STRUCTURE | Autonom | $^1$H-NMR | MS (APCI (M+H)$^+$) |
|---|---|---|---|---|
| 1 | 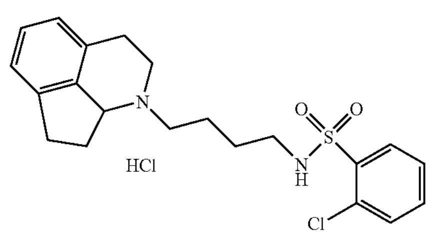 | 2-Chloro-N-[4-(2,2a,4,5-tetrahydro-1H-3-aza-acenaphthylen-3-yl)-butyl]-benzenesulfonamide hydrochloride | | 405 |

-continued

| N° | STRUCTURE | Autonom | ¹H-NMR | MS (APCI (M + H)⁺) |
|---|---|---|---|---|
| 2 | 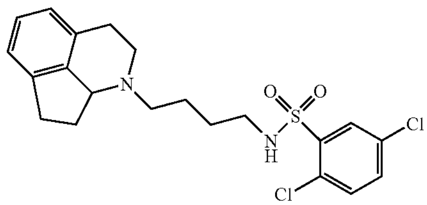 | 2,5-Dichloro-N-[4-(2,2a,4,5-tetrahydro-1H-3-aza-acenaphthylen-3-yl)-butyl]-benzenesulfonamide | 1H NMR (400 MHz, DMSO-D6) δ ppm 1.41 (m, 5 H) 2.04 (m, 1 H) 2.15 (m, 1 H) 2.30 (m, 1 H) 2.54 (m, 1 H) 2.70 (m, 3 H) 2.76 (m, 1 H) 2.88 (s, 2 H) 3.08 (m, 1 H) 3.24 (m, 1 H) 6.87 (d, J = 7.23 Hz, 1 H) 7.00 (m, 2 H) 7.65 (m, 2 H) 7.87 (d, J = 1.86 Hz, 1 H) 8.12 (s, 1 H) | 439 |
| 3 | 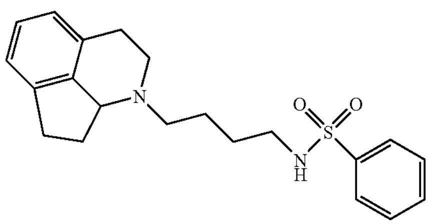 | N-[4-(2,2a,4-5-Tetrahydro-1H-3-aza-acenaphthylen-3-yl)-butyl]-benzenesulfonamide | | 371 |
| 4 | 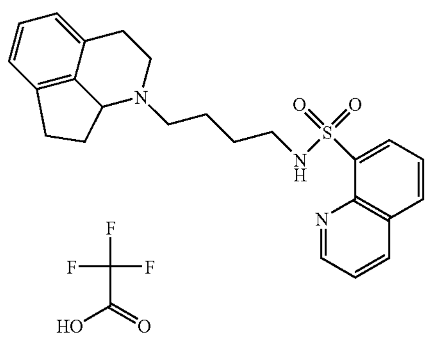 | Quinoline-8-sulfonic acid[4-(2,2a,4-5-tetrahydro-1H-3-aza-acenaphthylen-3-yl)-butyl]-amide trifluoroacetate | | 422 |
| 5 | 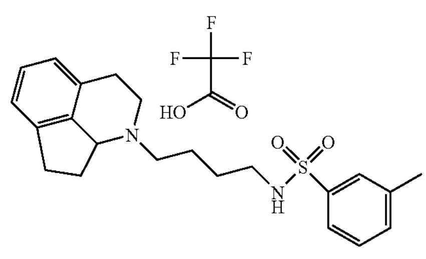 | 3-Methyl-N-[4-(2,2a,4-5-tetrahydro-1H-3-aza-acenaphthylen-3-yl)-butyl]-benzenesulfonamide trifluoroacetate | | 385 |
| 6 | 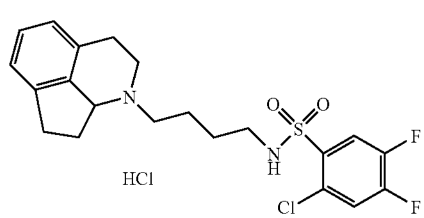 | 2-Chloro-4,5-difluoro-N-[4-(2,2a,4-5-tetrahydro-1H-3-aza-acenaphthylen-3-yl)-butyl]-benzenesulfonamide hydrochloride | | 441 |

-continued

| N° | STRUCTURE | Autonom | $^1$H-NMR | MS (APCI (M + H)$^+$) |
|---|---|---|---|---|
| 7 | (structure with HCl) | 4-Chloro-2,5-dimethyl-N-[4-(2,2a,4-5-tetrahydro-1H-3-aza-acenaphthylen-3-yl)-butyl]-benzenesulfonamide hydrochloride | 1H NMR (300 MHz, DMSO-D6) δ ppm 1.25 (m, 1 H) 1.47 (m, 2 H) 1.70 (m, 2 H) 1.98 (m, 1 H) 2.34 (s, 3 H) 2.51 (s, 3 H) 2.60 (m, 1 H) 2.79 (q, J = 6.64 Hz, 2 H) 2.88 (d, J = 9.67 Hz, 2 H) 3.09 (m, 3 H) 3.39 (m, 1 H) 3.77 (d, J = 9.96 Hz, 1 H) 4.55 (m, 1 H) 7.08 (d, J = 7.18 Hz, 1 H) 7.16 (d, J = 7.03 Hz, 1 H) 7.26 (t, J = 7.54 Hz, 1 H) 7.51 (s, 1 H) 7.76 (s, 1 H) 7.81 (t, J = 5.86 Hz, 1 H) 10.16 (br, 1 H) | 433 |
| 8 | (structure with HCl) | 3-Chloro-4-fluoro-N-[4-(2,2a,4-5-tetrahydro-1H-3-aza-acenaphthylen-3-yl)-butyl]-benzenesulfonamide hydrochloride | | 423 |
| 9 | (structure with HCl) | 2,4,5-Trichloro-N-[4-(2,2a,4-5-tetrahydro-1H-3-aza-acenaphthylen-3-yl)-butyl]-benzenesulfonamide hydrochloride | | 473 |
| 10 | (structure with HCl) | 5-fluoro-2-methyl-N-[4-(2,2a,4-5-tetrahydro-1H-3-aza-acenaphthylen-3-yl)-butyl]-benzenesulfonamide hydrochloride | | 403 |
| 11 | (structure) | Naphthalene-1-sulfonic acid[4-(2,2a,4-5-tetrahydro-1H-3-aza-acenaphthylen-3-yl)-butyl]-amide | | 421 |

-continued

| N° | STRUCTURE | Autonom | ¹H-NMR | MS (APCI (M + H)⁺) |
|---|---|---|---|---|
| 12 | 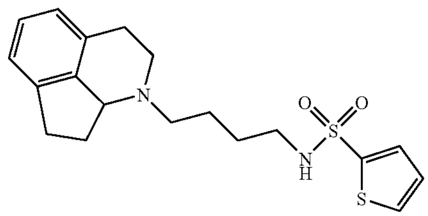 | Thiophene-2-sulfonic acid[4-(2,2a,4-5-tetrahydro-1H-3-aza-acenaphthylen-3-yl)-butyl]-amide | | 377 |
| 13 | 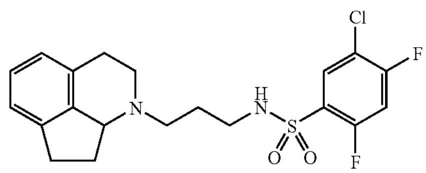 | 5-Chloro-2,4-difluoro-N-[3-(2,2a,4-5-tetrahydro-1H-3-aza-acenaphthylen-3-yl)-propyl]-benzenesulfonamide hydrochloride | ¹H NMR (300 MHz, DMSO-D6) δ ppm 1.97 (m, 4 H) 2.57 (m, 1 H) 2.88 (m, 2 H) 3.00 (q, J = 6.35 Hz, 2 H) 3.10 (m, 3 H) 3.40 (m, 1 H) 3.78 (m, 1 H) 4.59 (m, 1 H) 7.08 (d, J = 7.47 Hz, 1 H) 7.16 (m, 1 H) 7.25 (m, 1 H) 7.92 (m, 2 H) 8.36 (t, J = 5.78 Hz, 1 H) 10.26 (br, 1 H) | 427 |
| 14 | 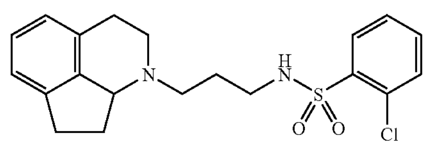 | 2-Chloro-N-[3-(2,2a,4-5-tetrahydro-1H-3-aza-acenaphthylen-3-yl)-propyl]-benzenesulfonamide hydrochloride | | 391 |
| 15 | 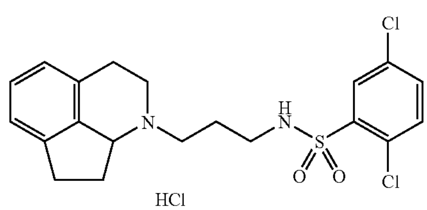 | 2,5-Dichloro-N-[3-(2,2a,4-5-tetrahydro-1H-3-aza-acenaphthylen-3-yl)-propyl]-benzenesulfonamide hydrochloride | | 425 |
| 16 | 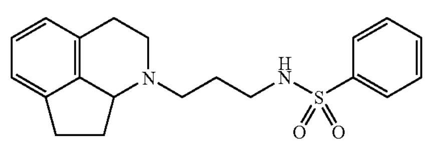 | N-[3-(2,2a,4-5-tetrahydro-1H-3-aza-acenaphthylen-3-yl)-propyl]-benzenesulfonamide hydrochloride | | 357 |
| 17 | 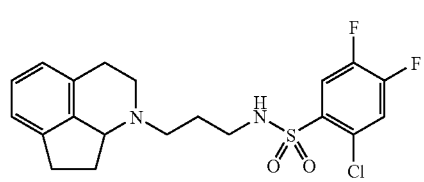 | 2-Chloro-4,5-difluoro-N-[3-(2,2a,4-5-tetrahydro-1H-3-aza-acenaphthylen-3-yl)-propyl]-benzenesulfonamide hydrochloride | | 427 |

-continued

| N° | STRUCTURE | Autonom | ¹H-NMR | MS (APCI (M + H)⁺) |
|---|---|---|---|---|
| 18 | 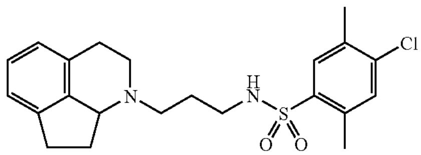 | 4-Chloro-2,5-dimethyl-N-[3-(2,2a,4-5-tetrahydro-1H-3-aza-acenaphthylen-3-yl)-propyl]-benzenesulfonamide hydrochloride | | 419 |
| 19 | 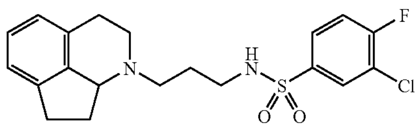 | 3-Chloro-4-fluoro-N-[3-(2,2a,4-5-tetrahydro-1H-3-aza-acenaphthylen-3-yl)-propyl]-benzenesulfonamide hydrochloride | | 409 |
| 20 | 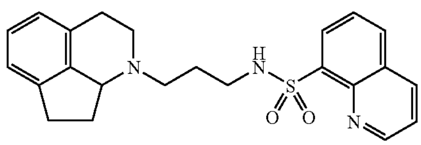 | Quinolin-8-sulfonic acid[3-(2,2a,4-5-tetrahydro-1H-3-aza-acenaphthylen-3-yl)-propyl]-amide | | 408 |
| 21 | 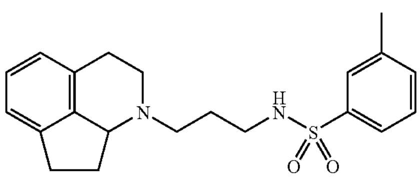 | 3-Methyl-N-[3-(2,2a,4-5-tetrahydro-1H-3-aza-acenaphthylen-3-yl)-propyl]-benzenesulfonamide hydrochloride | | 371 |
| 22 | 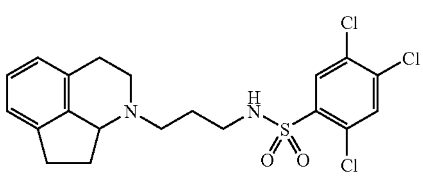 | 2,4,5-Trichloro-N-[3-(2,2a,4-5-tetrahydro-1H-3-aza-acenaphthylen-3-yl)-propyl]-benzenesulfonamide | | 459 |
| 23 | 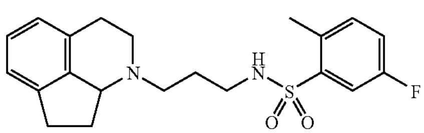 | 5-Fluoro-2-methyl-N-[3-(2,2a,4-5-tetrahydro-1H-3-aza-acenaphthylen-3-yl)-propyl]-benzenesulfonamide hydrochloride | | 389 |
| 24 | 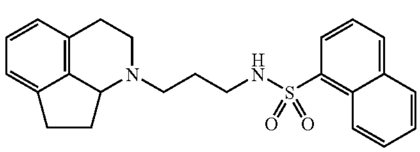 | Naphthalene-1-sulfonic acid[3-(2,2a,4-5-tetrahydro-1H-3-aza-acenaphthylen-3-yl)-propyl]-amide | | 407 |
| 25 | 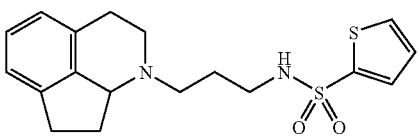 | Thiophene-2-sulfonic acid[3-(2,2a,4-5-tetrahydro-1H-3-aza-acenaphthylen-3-yl)-propyl]-amide hydrochloride | | 363 |

| N° | STRUCTURE | Autonom | ¹H-NMR | MS (APCI (M + H)⁺) |
|----|-----------|---------|--------|---------------------|
| 26 | 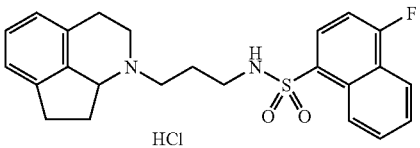 HCl | 4-Fluoro-naphthalene-1-sulfonic acid[3-(2,2a,4-5-tetrahydro-1H-3-aza-acenaphthylen-3-yl)-propyl]-amide hydrochloride | | 425 |
| 27 | 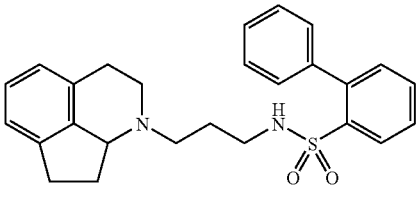 HCl | Biphenyl-2-sulfonic acid[3-(2,2a,4-5-tetrahydro-1H-3-aza-acenaphthylen-3-yl)-propyl]-amide hydrochloride | | 433 |
| 28 | 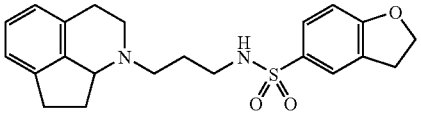 HCl | 2,3-Dihydro-benzofuran-5-sulfonic acid[3-(2,2a,4-5-tetrahydro-1H-3-aza-acenaphthylen-3-yl)-propyl]-amide hydrochloride | 1H NMR (300 MHz, DMSO-D6) δ ppm 1.92 (m, 4 H) 2.56 (m, 1 H) 2.83 (m, 4 H) 3.09 (m, 3 H) 3.24 (m, 2 H) 3.39 (m, 1 H) 3.77 (d, J = 11.13 Hz, 1 H) 4.62 (m, 3 H) 6.93 (d, J = 8.49 Hz, 1 H) 7.08 (d, J = 7.47 Hz, 1 H) 7.17 (m, 1 H) 7.26 (t, J = 7.47 Hz, 1 H) 7.60 (m, 3 H) 10.27 (br, 1 H) | 399 |
| 29 | 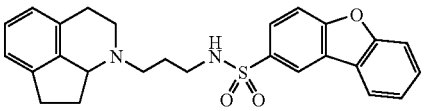 HCl | Dibenzofuran-2-sulfonic acid [3-(2,2a,4-5-tetrahydro-1H-3-aza-acenaphthylen-3-yl)-propyl]-amide hydrochloride | | 447 |
| 30 | 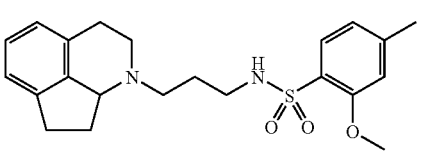 HCl | 2-Methoxy-4-methyl-N-[3-(2,2a,4-5-tetrahydro-1H-3-aza-acenaphthylen-3-yl)-propyl]-benzenesulfonamide hydrochloride | | 401 |
| 31 |  HCl | 5-Isoxazol-5-yl-thiophene-2-sulfonic acid[3-(2,2a,4-5-tetrahydro-1H-3-aza-acenaphthylen-3-yl)-propyl]-amide hydrochloride | 1H NMR (300 MHz, DMSO-D6) δ ppm 1.95 (m, 3 H) 2.56 (m, 1 H) 2.86 (m, 2 H) 3.02 (m, 2 H) 3.11 (m, 3 H) 3.41 (m, 2 H) 3.80 (d, J = 10.74 Hz, 1 H) 4.60 (m, 1 H) 7.12 (m, 3 H) 7.26 (t, J = 7.45 Hz,1 H) 7.71 (d, J = 3.91 Hz, 1 H) 7.78 (d, J = 3.91 Hz, 1 H) 8.34 (t, J = 5.74 Hz, 1 H) 8.74 (d, J = 1.95 Hz, 1 H) 10.31 (br, 1 H) | 430 |

-continued

| N° | STRUCTURE | Autonom | ¹H-NMR | MS (APCI (M + H)⁺) |
|---|---|---|---|---|
| 32 | 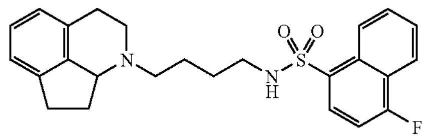 | 4-Fluoro-naphthalene-1-sulfonic acid[4-(2,2a,4-5-tetrahydro-1H-3-aza-acenaphthylen-3-yl)-butyl]-amide | | 439 |
| 33 | 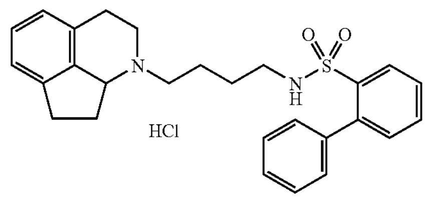 | Biphenyl-2-sulfonic acid[4-(2,2a,4-5-tetrahydro-1H-3-aza-acenaphthylen-3-yl)-butyl]-amide hydrochloride | | 447 |
| 34 | 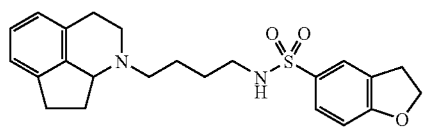 | 2,3-Dihydro-benzofuran-5-sulfonic acid[4-(2,2a,4-5-tetrahydro-1H-3-aza-acenaphthylen-3-yl)-butyl]-amide hydrochloride | | 413 |
| 35 | 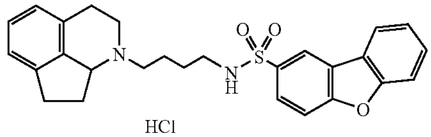 | Dibenzofuran-2-sulfonic acid[4-(2,2a,4-5-tetrahydro-1H-3-aza-acenaphthylen-3-yl)-butyl]-amide hydrochloride | | 461 |
| 36 | 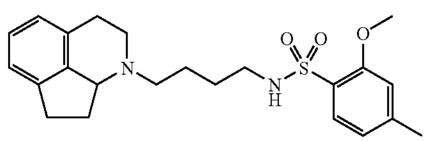 | 2-Methoxy-4-methyl-N-[4-(2,2a,4-5-tetrahydro-1H-3-aza-acenaphthylen-3-yl)-butyl]-benzenesulfonamide hydrochloride | | 415 |
| 37 | 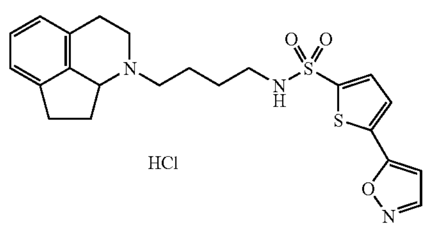 | 5-Isoxazol-5-yl-thiophene-2-sulfonic acid[4-(2,2a,4-5-tetrahydro-1H-3-aza-acenaphthylen-3-yl)-butyl]-amide hydrochloride | ¹H NMR (300 MHz, DMSO-D6) δppm 1.51 (m, 2 H) 1.72 (m, 2 H) 1.99 (m, 1 H) 2.63 (m, 1 H) 2.88 (m, 4 H) 3.08 (m, 3 H) 3.39 (m, 2 H) 3.81 (m, 1 H) 4.54 (m, 1 H) 7.09 (m, 2 H) 7.16 (d, J = 7.82 Hz, 1 H) 7.26 (t, J = 7.47 Hz, 1 H) 7.69 (d, J = 3.95 Hz, 1 H) 7.76 (d, J = 3.95 Hz, 1 H) 8.20 (t, J = 5.71 Hz, 1 H) 8.73 (d, J = 2.05 Hz, 1 H) 10.18 (br, 1 H) | 444 |
| 38 | 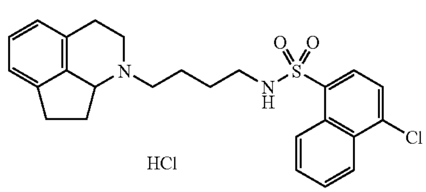 | 4-Chloro-naphthalene-1-sulfonic acid[3-(2,2a,4-5-tetrahydro-1H-3-aza-acenaphthylen-3-yl)-butyl]-amide | | 455 |

-continued

| N° | STRUCTURE | Autonom | ¹H-NMR | MS (APCI (M + H)⁺) |
|----|-----------|---------|--------|---------------------|
| 39 | 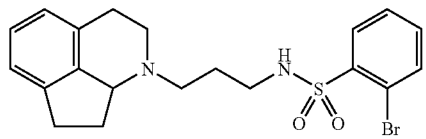 | 2-Bromo-N-[3-(2,2a,4-5-tetrahydro-1H-3-aza-acenaphthylen-3-yl)-propyl]-benzenesulfonamide | | 435 |
| 40 | 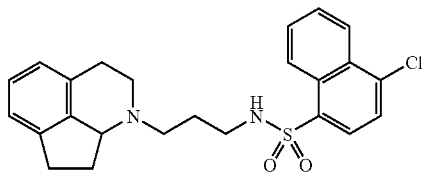 | 4-Chloro-naphthalene-1-sulfonic acid[3-(2,2a,4-5-tetrahydro-1H-3-aza-acenaphthylen-3-yl)-propyl]-amide | | 441 |
| 41 | 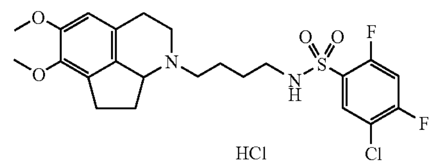 | 5-Chloro-N-[4-(7,8-dimethoxy-2,2a,4-5-tetrahydro-1H-3-aza-acenaphthylen-3-yl)-butyl]-2,4-difluoro-benzene sulfonamide hydrochloride | | 501 |
| 42 | 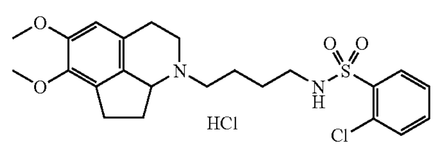 | 2-Chloro-N-[4-(7,8-dimethoxy-2,2a,4-5-tetrahydro-1H-3-aza-acenaphthylen-3-yl)-butyl]-benzenesulfonamide hydrochloride | | 465 |
| 43 | 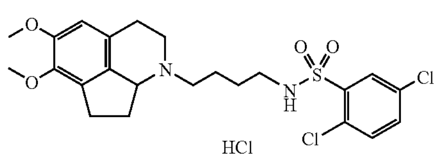 | 2,5-Dichloro-N-[4-(7,8-dimethoxy-2,2a,4-5-tetrahydro-1H-3-aza-acenaphthylen-3-yl)-butyl]-benzenesulfonamide hydrochloride | | 499 |
| 44 | 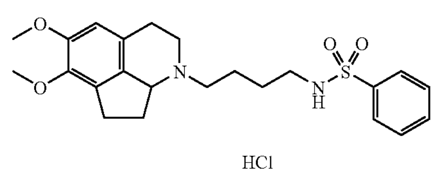 | N-[4-(7,8-dimethoxy-2,2a,4-5-tetrahydro-1H-3-aza-acenaphthylen-3-yl)-butyl]-benzenesulfonamide hydrochloride | | 431 |
| 45 | 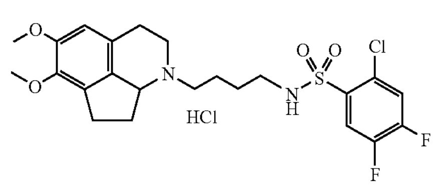 | 2-Chloro-N-[4-(7,8-dimethoxy-2,2a,4-5-tetrahydro-1H-3-aza-acenaphthylen-3-yl)-butyl]-4,5-difluoro-benzene sulfonamide hydrochloride | | 501 |
| 46 | 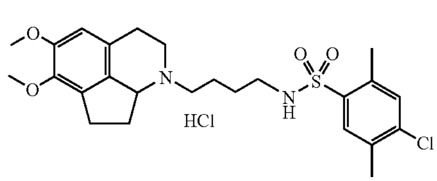 | 4-Chloro-N-[4-(7,8-dimethoxy-2,2a,4-5-tetrahydro-1H-3-aza-acenaphthylen-3-yl)-butyl]-2,5-dimethyl-benzene sulfonamide hydrochloride | | 493 |
| 47 | 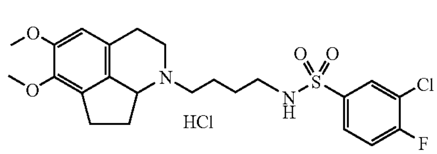 | 3-Chloro-N-[4-(7,8-dimethoxy-2,2a,4-5-tetrahydro-1H-3-aza-acenaphthylen-3-yl)-butyl]-4-fluoro-benzene sulfonamide hydrochloride | | 483 |

-continued

| N° | STRUCTURE | Autonom | ¹H-NMR | MS (APCI (M + H)⁺) |
|---|---|---|---|---|
| 48 | 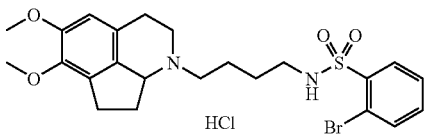 | 2-Bromo-N-[4-(7,8-dimethoxy-2,2a,4-5-tetrahydro-1H-3-aza-acenaphthylen-3-yl)-butyl]-benzene sulfonamide hydrochloride | | 509 |
| 49 | 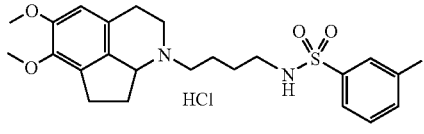 | N-[4-(7,8-dimethoxy-2,2a,4-5-tetrahydro-1H-3-aza-acenaphthylen-3-yl)-butyl]-3-methyl-benzene sulfonamide hydrochloride | | 445 |
| 50 | 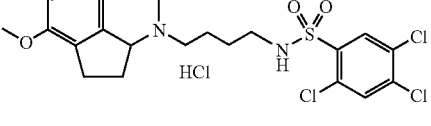 | 2,4,5-Trichloro-N-[4-(7,8-dimethoxy-2,2a,4-5-tetrahydro-1H-3-aza-acenaphthylen-3-yl)-butyl]-benzene sulfonamide hydrochloride | | 533 |
| 51 | 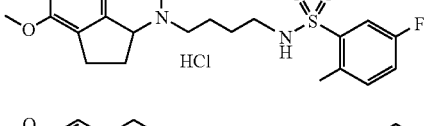 | N-[4-(7,8-dimethoxy-2,2a,4-5-tetrahydro-1H-3-aza-acenaphthylen-3-yl)-butyl]-5-fluoro-2-methyl-benzene sulfonamide hydrochloride | | 463 |
| 52 | 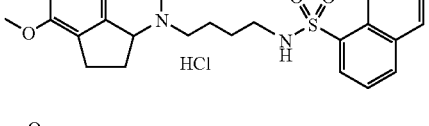 | Naphtalene-1-sulfonic acid [4-(7,8-dimethoxy-2,2a,4-5-tetrahydro-1H-3-aza-acenaphthylen-3-yl)-butyl]-amide hydrochloride | | 481 |
| 53 | 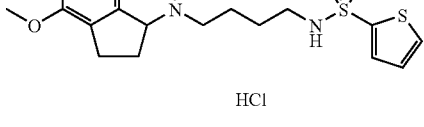 | Thiophene-2-sulfonic acid [4-(7,8-dimethoxy-2,2a,4-5-tetrahydro-1H-3-aza-acenaphthylen-3-yl)-butyl]-amide hydrochloride | | 437 |
| 54 | 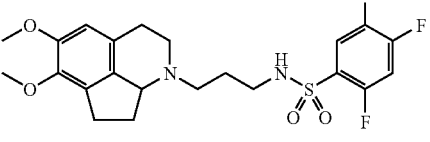 | 5-Chloro-N-[3-(7,8-dimethoxy-2,2a,4-5-tetrahydro-1H-3-aza-acenaphthylen-3-yl)-propyl]-2,4-difluoro-benzene sulfonamide hydrochloride | | 487 |
| 55 | 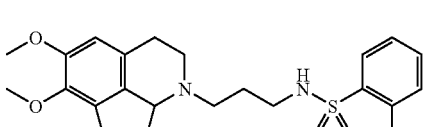 | 2-Chloro-N-[3-(7,8-dimethoxy-2,2a,4-5-tetrahydro-1H-3-aza-acenaphthylen-3-yl)-propyl]-benzene sulfonamide hydrochloride | | 451 |
| 56 | 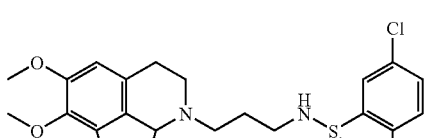 | 2,5-Dichloro-N-[3-(7,8-dimethoxy-2,2a,4-5-tetrahydro-1H-3-aza-acenaphthylen-3-yl)-propyl]-benzene sulfonamide hydrochloride | | 485 |

-continued

| N° | STRUCTURE | Autonom | ¹H-NMR | MS (APCI (M + H)⁺) |
|---|---|---|---|---|
| 57 | 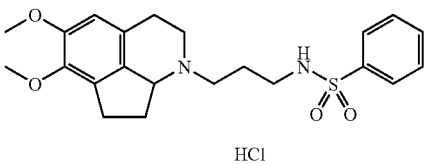 HCl | N-[3-(7,8-dimethoxy-2,2a,4-5-tetrahydro-1H-3-aza-acenaphthylen-3-yl)-propyl]-benzene sulfonamide hydrochloride | ¹H NMR (300 MHz, DMSO-D6) δppm 1.89 (m, 4 H) 2.54 (m, 1 H) 2.84 (m, 3 H) 3.00 (m, 4 H) 3.41 (m, 1 H) 3.71 (m, 1 H) 3.72 (s, 3 H) 3.75 (s, 3 H) 4.49 (m, 1 H) 6.77 (s, 1 H) 7.63 (m, 3 H) 7.80 (m, 3 H) 10.05 (br, 1 H) | 417 |
| 58 | 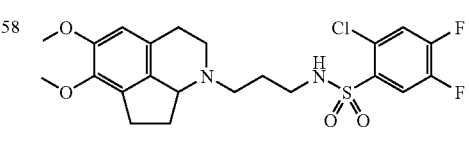 HCl | 2-Chloro-N-[3-(7,8-dimethoxy-2,2a,4-5-tetrahydro-1H-3-aza-acenaphthylen-3-yl)-propyl]-4,5-difluoro-benzene sulfonamide hydrochloride | ¹H NMR (300 MHz, DMSO-D6) δppm 1.96 (s, 4 H) 2.58 (m, 1 H) 2.87 (m, 3 H) 2.99 (m, 4 H) 3.40 (m, 1 H) 3.72 (s, 3 H) 3.74 (s, 3 H) 3.75 (m, 1 H) 4.49 (d, J = 5.86 Hz, 1 H) 6.77 (s, 1 H) 8.01 (m, 2 H) 8.31 (t, J = 5.49 Hz, 1 H) 10.20 (br, 1 H) | 487 |
| 59 | 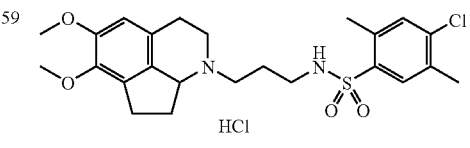 HCl | 4-Chloro-N-[3-(7,8-dimethoxy-2,2a,4-5-tetrahydro-1H-3-aza-acenaphthylen-3-yl)-propyl]-2,5-dimethyl-benzene sulfonamide hydrochloride | | 481 |
| 60 | 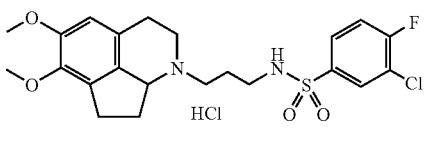 HCl | 3-Chloro-N-[3-(7,8-dimethoxy-2,2a,4-5-tetrahydro-1H-3-aza-acenaphthylen-3-yl)-propyl]-4-fluoro-benzene sulfonamide hydrochloride | | 469 |
| 61 | 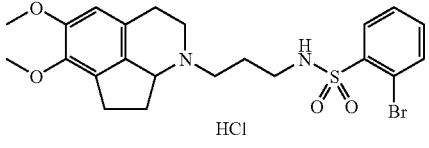 HCl | 2-Bromo-N-[3-(7,8-dimethoxy-2,2a,4-5-tetrahydro-1H-3-aza-acenaphthylen-3-yl)-propyl]-benzene sulfonamide hydrochloride | | 495 |
| 62 | 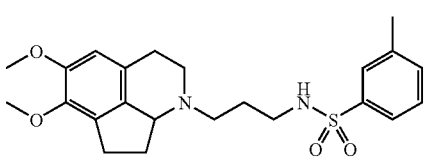 HCl | N-[3-(7,8-dimethoxy-2,2a,4-5-tetrahydro-1H-3-aza-acenaphthylen-3-yl)-propyl]-3-methyl-benzene sulfonamide hydrochloride | | 431 |
| 63 | 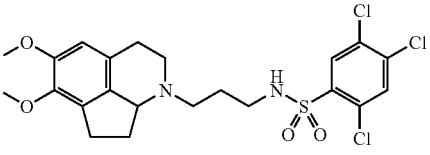 HCl | 2,4,5-Trichloro-N-[3-(7,8-dimethoxy-2,2a,4-5-tetrahydro-1H-3-aza-acenaphthylen-3-yl)-propyl]-benzene sulfonamide hydrochloride | | 521 |

-continued

| N° | STRUCTURE | Autonom | ¹H-NMR | MS (APCI (M + H)⁺) |
|---|---|---|---|---|
| 64 | 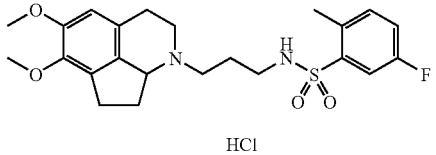 | N-[3-(7,8-dimethoxy-2,2a,4-5-tetrahydro-1H-3-aza-acenaphthylen-3-yl)-propyl]-5-fluoro-2-methyl-benzene sulfonamide hydrochloride | | 449 |
| 65 | 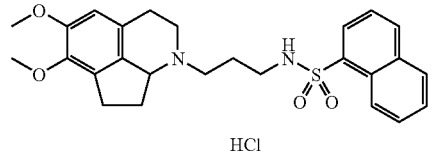 | Naphtalene-1-sulfonic acid [3-(7,8-dimethoxy-2,2a,4-5-tetrahydro-1H-3-aza-acenaphthylen-3-yl)-propyl]-amide hydrochloride | | 467 |
| 66 | 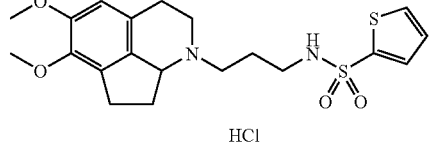 | Thiophene-2-sulfonic acid [3-(7,8-dimethoxy-2,2a,4-5-tetrahydro-1H-3-aza-acenaphthylen-3-yl)-propyl]-amide hydrochloride | | 423 |
| 67 | 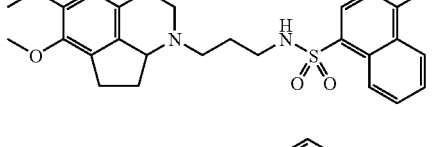 | 4-Fluoro-naphtalene-1-sulfonic acid [3-(7,8-dimethoxy-2,2a,4-5-tetrahydro-1H-3-aza-acenaphthylen-3-yl)-propyl]-amide | | 485 |
| 68 | 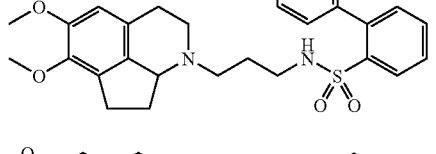 | Biphenyl-2-sulfonic acid[3-(7,8-dimethoxy-2,2a,4-5-tetrahydro-1H-3-aza-acenaphthylen-3-yl)-propyl]-amide | | 493 |
| 69 | 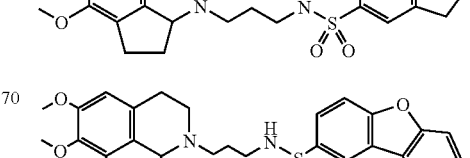 | 2,3-Dihydro-benzofuran-5-sulfonic acid[3-(7,8-dimethoxy-2,2a,4-5-tetrahydro-1H-3-aza-acenaphthylen-3-yl)-propyl]-amide | | 459 |
| 70 | 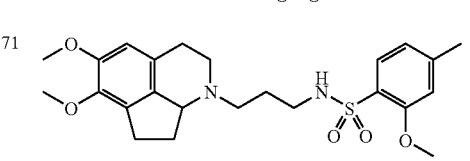 | Dibenzofuran-2-sulfonic acid[3-(7,8-dimethoxy-2,2a,4-5-tetrahydro-1H-3-aza-acenaphthylen-3-yl)-propyl]-amide hydrochloride | | 507 |
| 71 | 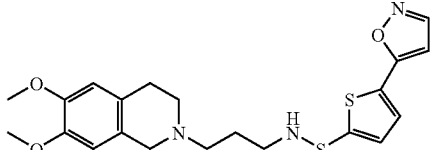 | N-[3-(7,8-Dimethoxy-2,2a,4-5-tetrahydro-1H-3-aza-acenaphthylen-3-yl)-propyl]-2-methoxy-4-methyl-benzenesulfonamide | | 461 |
| 72 | 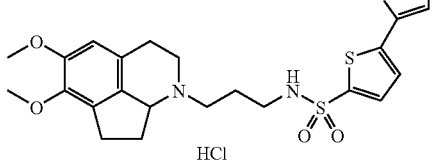 | 5-Isoxazol-5-yl-thiophene-2-sulfonic acid[3-(7,8-dimethoxy-2,2a,4-5-tetrahydro-1H-3-aza-acenaphthylen-3-yl)-propyl]-amide hydrochloride | | 490 |

| N° | STRUCTURE | Autonom | ¹H-NMR | MS (APCI (M + H)⁺) |
|---|---|---|---|---|
| 73 | 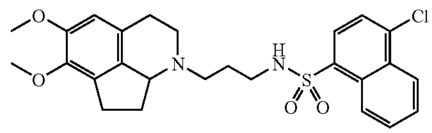 | 4-Chloro-naphtalene-1-sulfonic acid [3-(7,8-dimethoxy-2,2a,4-5-tetrahydro-1H-3-aza-acenaphthylen-3-yl)-propyl]-amide | | 501 |
| 74 | HCl | 5-Chloro-2,4-difluoro-N-[4-(2,2a,4,5-tetrahydro-1H-3-aza-acenaphthylen-3-yl)-butyl]-benzenesulfonamide hydrochloride | | 441 |
| 75 | HCl | 4-Chloro-N-ethyl-2,5-dimethoxy-N-[3-(2,2a,4,5-tetrahydro-1H-3-aza-acenaphthylen-3-yl)-propyl]-benzenesulfo-Namide hydrochloride | | 447 |
| 76 | HCl | 4-Chloro-N-ethyl-N-[3-(7-methoxy-2,2a,4,5-tetrahydro-1H-3-aza-acenaphthylen-3-yl)-propyl]-2,5-dimethyl-benzenesulfonamide hydrochloride | | 477 |
| 77 | HCl | 4-Chloro-N-[3-(7,8-dimethoxy-2,2a,4,5-tetrahydro-1H-3-aza-acenaphthylen-3-yl)-propyl]-N-ethyl-2,5-dimethyl-benzenesulfonamide hydrochloride | | 507 |
| 78 | HCl | 2,3-Dihydro-benzofuran-5-sulfonic acid ethyl-[3-(2,2a,4,5-tetrahydro-1H-3-aza-acenaphthylen-3-yl)-propyl]-amide hydrochloride | | 427 |
| 79 | HCl | 2,3-Dihydro-benzofuran-5-sulfonic acid [3-(7,8-dimethoxy-2,2a,4,5-tetrahydro-1H-3-aza-acenaphthylen-3-yl)-propyl]-ethylamide hydrochloride | | 487 |
| 80 | HCl | 2,5-Dichloro-N-[3-(7,8-dimethoxy-2,2a,4,5-tetrahydro-1H-3-aza-acenaphthylen-3-yl)-propyl]-N-ethyl-benzene sulfonamide hydrochloride | 1H NMR (300 MHz, DMSO-d₆) δppm 1.03 (t, J = 7.03 Hz, 3 H) 1.99 (m, 4 H) 2.54 (m, 1 H) 2.88 (m, 2 H) 3.03 (m, 4 H) 3.36 (q, J = 7.03 Hz, 2 H) 3.44 (m, 2 H) 3.73 (s, 3 H) 3.75 (s, 3 H) 3.79 (m, 1 H) 4.51 (q, J = 9.37 Hz, 1 H) 6.78 (s, 1 H) 7.77 (td, J = 8.17, 5.35 Hz, 2 H) 7.96 (d, J = 1.90 Hz, 1 H) 10.23 (br, 1 H) | 513 |

| N° | STRUCTURE | Autonom | ¹H-NMR | MS (APCI (M + H)⁺) |
|---|---|---|---|---|
| 81 | 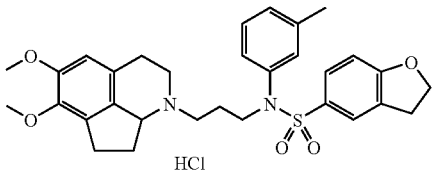 | 2,3-Dihydro-benzofuran-5-sulfonic acid [3-(7,8-dimethoxy-2,2a,4,5-tetrahydro-1H-3-aza-acenaphthylen-3-yl)-propyl]-m-tolyl-amide hydrochloride | | 549 |
| 82 | 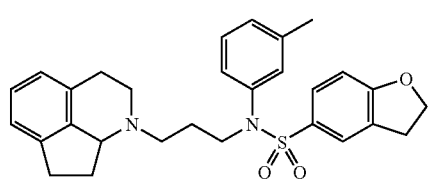 | 2,3-Dihydro-benzofuran-5-sulfonic acid [3-(2,2a,4,5-tetrahydro-1H-3-aza-acenaphthylen-3-yl)-propyl]-m-tolyl-amide hydrochloride | | 489 |
| 83 | 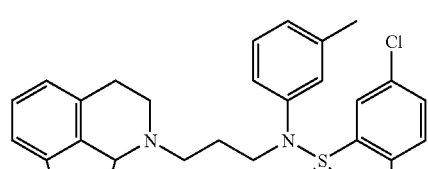 | 2,5-Dichloro-N-[3-(2,2a,4,5-tetrahydro-1H-3-aza-acenaphthylen-3-yl)-propyl]-N-m-tolyl-benzenesulfonamide hydrochloride | | 515 |
| 84 | 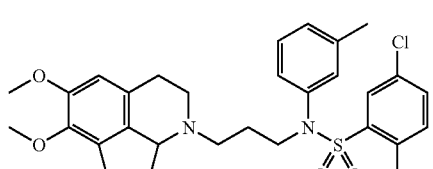 | 2,5-Dichloro-N-[3-(7,8-dimethoxy-2,2a,4,5-tetrahydro-1H-3-aza-acenaphthylen-3-yl)-propyl]-N-m-tolyl-benzenesulfonamide hydrochloride | | 575 |
| 85 | 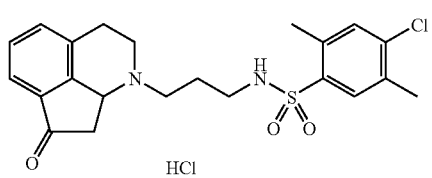 | 4-Chloro-2,5-dimethyl-N-[3-(1-oxo-2,2a,4,5-tetrahydro-1H-3-aza-acenaphthylen-3-yl)-propyl]-benzenesulfonamide hydrochloride | | 433 |
| 86 | 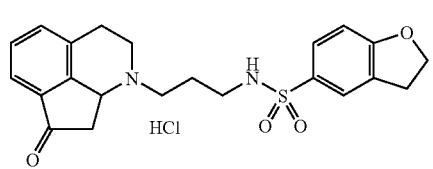 | 2,3-Dihydro-benzofuran-5-sulfonic acid [3-(1-oxo-2,2a,4,5-tetrahydro-1H-3-aza-acenaphthylen-3-yl)-propyl]-amide hydrochloride | | 413 |

-continued

| N° | STRUCTURE | Autonom | $^1$H-NMR | MS (APCI (M + H)$^+$) |
|---|---|---|---|---|
| 87 | 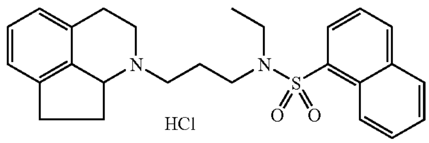 | Naphthalene-1-sulfonic acid ethyl-[3-(2,2a,4,5-tetrahydro-1H-3-aza-acenaphthylen-3-yl)-propyl]-amide hydrochloride | 1H NMR (300 MHz, DMSO-d$_6$) δ ppm 1.01 (t, J = 6.96 Hz, 3 H) 2.01 (m, 4 H) 2.41 (m, 1 H) 2.87 (d, J = 8.64 Hz, 2 H) 3.05 (m, 3 H) 3.39 (m, 5 H) 3.80 (m, 1 H) 4.51 (m, 1 H) 7.08 (d, J = 7.32 Hz, 1 H) 7.16 (m, 1 H) 7.27 (t, J = 7.18 Hz, 1 H) 7.70 (m, 3 H) 8.12 (d, J = 8.35 Hz, 2 H) 8.27 (d, J = 7.91 Hz, 1 H) 8.54 (d, J = 8.64 Hz, 1 H) 10.25 (br, 1 H) | 435 |
| 88 | 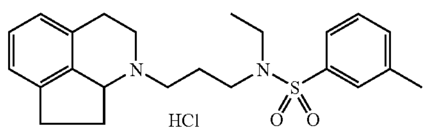 | N-Ethyl-3-methyl-N-[3-(2,2a,4,5-tetrahydro-1H-3-aza-acenaphthylen-3-yl)-propyl]-benzenesulfonamide hydrochloride | 1H NMR (300 MHz, DMSO-d$_6$) δ ppm 1.03 (t, J = 6.96 Hz, 3 H) 2.04 (m, 4 H) 2.40 (s, 3 H) 2.58 (m, 1 H) 2.90 (d, J = 7.91 Hz, 2 H) 3.16 (m, 6 H) 3.42 (m, 2 H) 3.85 (d, J = 11.86 Hz, 1 H) 4.63 (q, J = 9.28 Hz, 1 H) 7.09 (d, J = 7.47 Hz, 1 H) 7.17 (m, 1 H) 7.27 (t, J = 7.40 Hz, 1 H) 7.50 (d, J = 4.83 Hz, 2 H) 7.60 (m, 2 H) 10.40 (br, 1 H) | 399 |
| 89 | 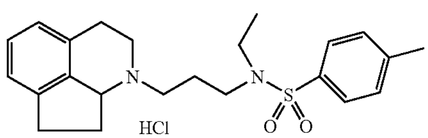 | N-Ethyl-4-methyl-N-[3-(2,2a,4,5-tetrahydro-1H-3-aza-acenaphthylen-3-yl)-propyl]-benzenesulfonamide hydrochloride | 1H NMR (300 MHz, DMSO-d$_6$) δ ppm 1.02 (t, J = 7.10 Hz, 3 H) 2.04 (m, 4 H) 2.38 (s, 3 H) 2.58 (m, 1 H) 2.89 (m, 2 H) 3.12 (m, 5 H) 3.17 (q, J = 7.18 Hz, 2 H) 3.42 (m, 1 H) 3.85 (d, J = 10.99 Hz, 1 H) 4.63 (q, J = 9.52 Hz, 1 H) 7.09 (d, J = 7.47 Hz, 1 H) 7.17 (m, 1 H) 7.27 (t, J = 7.47 Hz, 1 H) 7.42 (d, J = 8.06 Hz, 2 H) 7.69 (d, J = 8.06 Hz, 2 H) 10.36 (br, 1 H) | 399 |
| 90 | 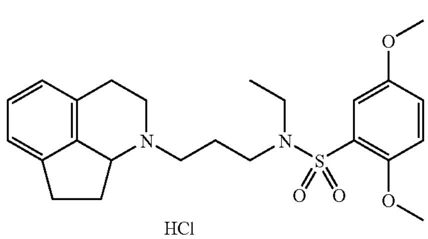 | N-Ethyl-2,5-dimethoxy-N-[3-(2,2a,4,5-tetrahydro-1H-3-aza-acenaphthylen-3-yl)-propyl]-benzenesulfonamide hydrochloride | | 445 |

| N° | STRUCTURE | Autonom | $^1$H-NMR | MS (APCI (M + H)$^+$) |
|---|---|---|---|---|
| 91 | 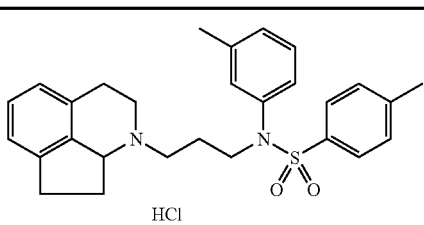 | 4-Methyl-N-[3-(2,2a,4,5-tetrahydro-1H-3-aza-acenaphthylen-3-yl)-propyl]-N-m-tolyl-benzenesulfonamide hydrochloride | | 461 |
| 92 | 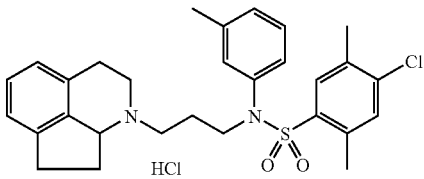 | 4-Chloro-2,5-dimethyl-N-[3-(2,2a,4,5-tetrahydro-1H-3-aza-acenaphthylen-3-yl)-propyl]-N-m-tolyl-benzenesulfonamide hydrochloride | | 509 |
| 93 | 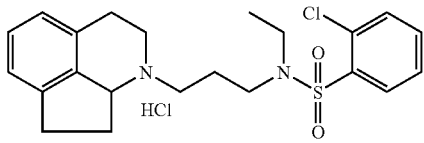 | 2-Chloro-N-ethyl-N-[3-(2,2a,4,5-tetrahydro-1H-3-aza-acenaphthylen-3-yl)-propyl]-benzenesulfonamide hydrochloride | | 419 |
| 94 | 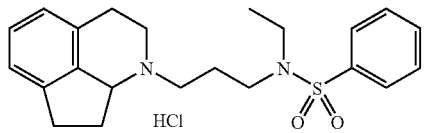 | N-Ethyl-N-[3-(2,2a,4,5-tetrahydro-1H-3-aza-acenaphthylen-3-yl)-propyl]-benzenesulfonamide hydrochloride | | 385 |
| 95 | 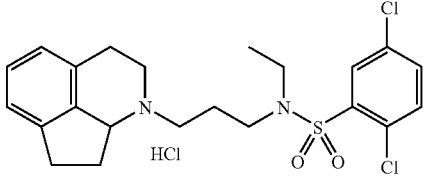 | 2,5-Dichloro-N-ethyl-N-[3-(2,2a,4,5-tetrahydro-1H-3-aza-acenaphthylen-3-yl)-propyl]-benzenesulfonamide hydrochloride | | 453 |
| 96 | 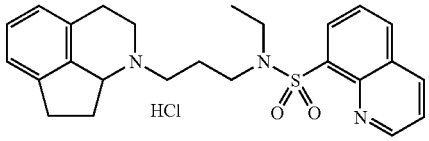 | Quinolin-8-sulfonic acid ethyl-[3-(2,2a,4,5-tetrahydro-1H-3-aza-acenaphthylen-3-yl)-propyl]-amide hydrochloride | | 436 |
| 97 | 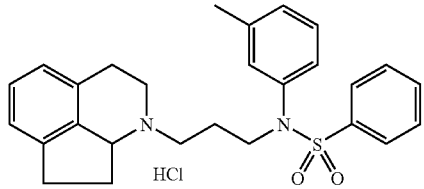 | N-[3-(2,2a,4,5-Tetrahydro-1H-3-aza-acenaphthylen-3-yl)-propyl]-N-m-tolyl-benzenesulfonamide hydrochloride | | 447 |
| 98 | 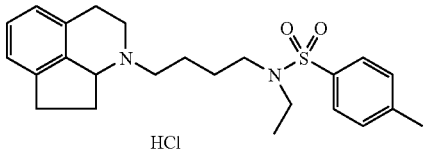 | N-Ethyl-4-methyl-N-[4-(2,2a,4,5-tetrahydro-1H-3-aza-acenaphthylen-3-yl)-butyl]-benzenesulfonamide hydrochloride | | 413 |

-continued

| N° | STRUCTURE | Autonom | ¹H-NMR | MS (APCI (M + H)⁺) |
|---|---|---|---|---|
| 99 | 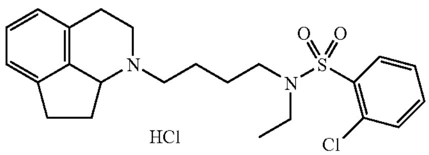 | 2-Chloro-N-ethyl-N-[4-(2,2a,4,5-tetrahydro-1H-3-aza-acenaphthylen-3-yl)-butyl]-benzenesulfonamide hydrochloride | | 433 |
| 100 | 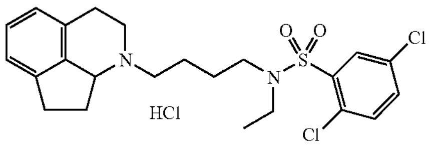 | 2,5-Dichloro-N-ethyl-[4-(2,2a,4,5-tetrahydro-1H-3-aza-acenaphthylen-3-yl)-butyl]-benzenesulfonamide hydrochloride | | 467 |
| 101 | 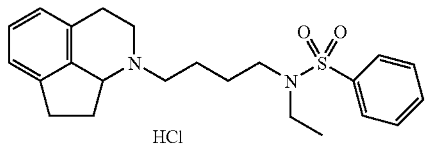 | N-Ethyl-N-[4-(2,2a,4,5-tetrahydro-1H-3-aza-acenaphthylen-3-yl)-butyl]-benzenesulfonamide hydrochloride | | 399 |
| 102 | 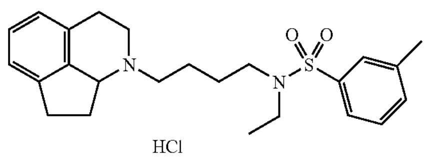 | N-Ethyl-3-methyl-N-[4-(2,2a,4,5-tetrahydro-1H-3-aza-acenaphthylen-3-yl)-butyl]-benzenesulfonamide hydrochloride | | 413 |
| 103 | 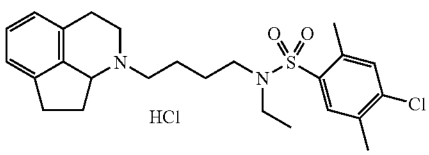 | 4-Chloro-N-ethyl-2,5-dimethyl-N-[4-(2,2a,4,5-tetrahydro-1H-3-aza-acenaphthylen-3-yl)-butyl]-benzenesulfonamide hydrochloride | | 461 |
| 104 | 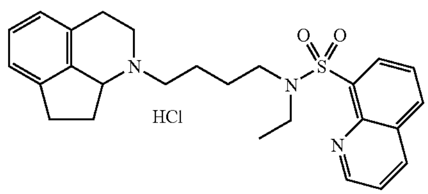 | Quinolin-8-sulfonic acid ethyl-[4-(2,2a,4,5-tetrahydro-1H-3-aza-acenaphthylen-3-yl)-butyl]-amide hydrochloride | | 450 |
| 105 | 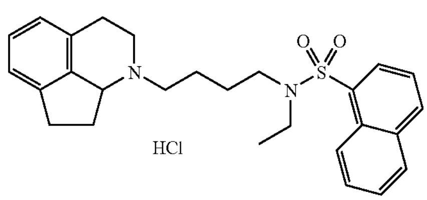 | Naphthalene-1-sulfonic acid ethyl-[4-(2,2a,4,5-tetrahydro-1H-3-aza-acenaphthylen-3-yl)-butyl]-amide hydrochloride | | 449 |
| 106 | 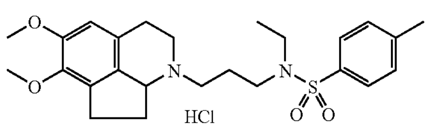 | N-[3-(7,8-Dimethoxy-2,2a,4,5-tetrahydro-1H-3-aza-acenaphthylen-3-yl)-propyl]-N-ethyl-4-methyl-benzenesulfonamide hydrochloride | | 459 |
| 107 | 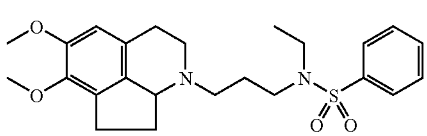 | N-[3-(7,8-Dimethoxy-2,2a,4,5-tetrahydro-1H-3-aza-acenaphthylen-3-yl)-propyl]-N-ethyl-benzenesulfonamide hydrochloride | | 445 |

-continued

| N° | STRUCTURE | Autonom | ¹H-NMR | MS (APCI (M + H)⁺) |
|---|---|---|---|---|
| 108 | 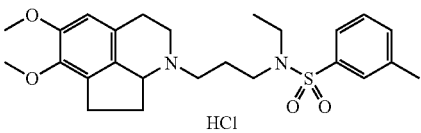 | N-[3-(7,8-Dimethoxy-2,2a,4,5-tetrahydro-1H-3-aza-acenaphthylen-3-yl)-propyl]-N-ethyl-3-methyl-benzenesulfonamide hydrochloride | | 459 |
| 109 | 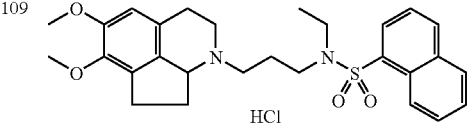 | Naphthalene-1-sulfonic acid [3-(7,8-dimethoxy-2,2a,4,5-tetrahydro-1H-3-aza-acenaphthylen-3-yl)-propyl]-ethyl-amide hydrochloride | | 495 |
| 110 | 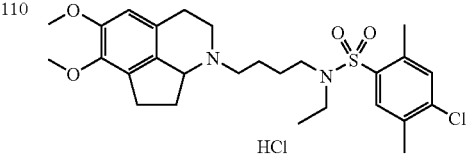 | 4-Chloro-N-[4-(7,8-dimethoxy-2,2a,4,5-tetrahydro-1H-3-aza-acenaphthylen-3-yl)-butyl]-N-ethyl-2,5-dimethyl-benzenesulfonamide hydrochloride | | 521 |
| 111 | 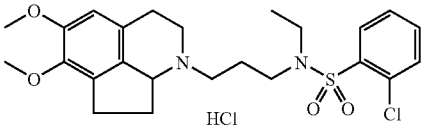 | 2-Chloro-N-[3-(7,8-dimethoxy-2,2a,4,5-tetrahydro-1H-3-aza-acenaphthylen-3-yl)-propyl]-N-ethyl-benzenesulfonamide hydrochloride | 1H NMR (300 MHz, DMSO-d₆) δ ppm 1.00 (t, J = 6.96 Hz, 3 H) 2.02 (m, 4 H) 2.54 (m, 1 H) 2.88 (m, 2 H) 3.03 (m, 4 H) 3.29 (q, J = 6.96 Hz, 2 H) 3.43 (m, 2 H) 3.72 (s, 3 H) 3.75 (s, 3 H) 3.78 (m, 1 H) 4.51 (q, J = 9.33 Hz, 1 H) 6.78 (s, 1 H) 7.56 (m, 1 H) 7.68 (qd, J = 8.01, 1.46 Hz, 2 H) 7.98 (m, 1 H) 10.24 (br, 1 H) | 479 |
| 112 | 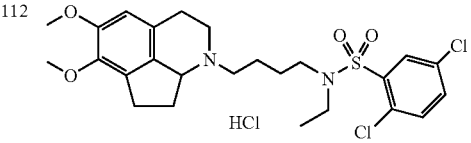 | 2,5-Dichloro-N-[3-(7,8-dimethoxy-2,2a,4,5-tetrahydro-1H-3-aza-acenaphthylen-3-yl)-butyl]-N-ethyl-benzenesulfonaamide hydrochloride | | 527 |
| 113 | 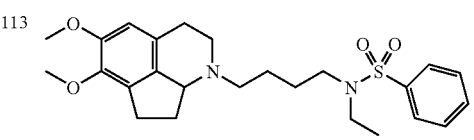 | N-[4-(7,8-Dimethoxy-2,2a,4,5-tetrahydro-1H-3-aza-acenaphthylen-3-yl)-butyl]-N-ethyl-benzenesulfonamide hydrochloride | | 459 |
| 114 | 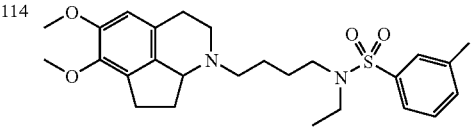 | N-[4-(7,8-Dimethoxy-2,2a,4,5-tetrahydro-1H-3-aza-acenaphthylen-3-yl)-butyl]-N-ethyl-3-methyl-benzenesulfonamide hydrochloride | | 473 |

| N° | STRUCTURE | Autonom | ¹H-NMR | MS (APCI (M + H)⁺) |
|---|---|---|---|---|
| 115 | 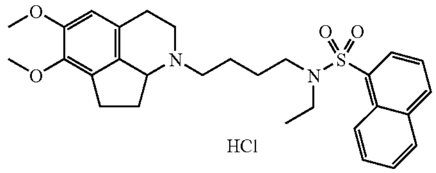 | Naphthalene-1-sulfonic acid [4-(7,8-dimethoxy-2,2a,4,5-tetrahydro-1H-3-aza-acenaphthylen-3-yl)-butyl]-ethyl-amide hydrochloride | | 509 |
| 116 | 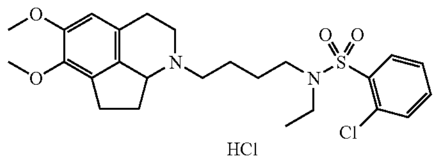 | 2-Chloro-N-[4-(7,8-dimethoxy-2,2a,4,5-tetrahydro-1H-3-aza-acenaphthylen-3-yl)-butyl]-N-ethyl-benzenesulfonamide hydrochloride | | 493 |
| 117 | 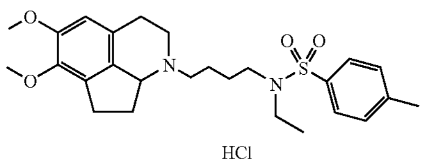 | N-[4-(7,8-dimethoxy-2,2a,4,5-tetrahydro-1H-3-aza-acenaphthylen-3-yl)-butyl]-N-ethyl--4-methyl-benzenesulfonamide hydrochloride | | 473 |
| 118 | 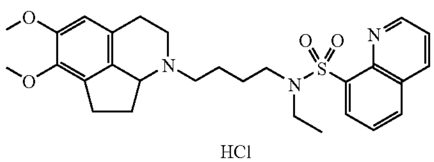 | Quinolin-8-sulfonic acid [4-(7,8-dimethoxy-2,2a,4,5-tetrahydro-1H-3-aza-acenaphthylen-3-yl)-butyl]-ethyl-amide hydrochloride | | 510 |
| 119 | 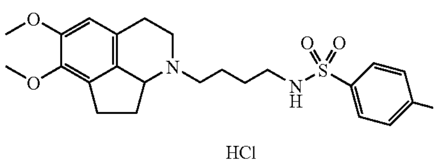 | N-[4-(7,8-Dimethoxy-2,2a,4,5-tetrahydro-1H-3-aza-acenaphthylen-3-yl)-butyl]-4-methyl-benzenesulfonamide hydrochloride | | 445 |
| 120 | 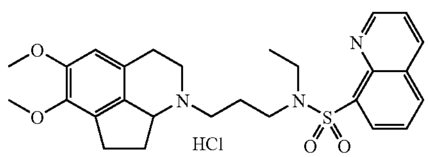 | Quinolin-8-sulfonic acid [3-(7,8-dimethoxy-2,2a,4,5-tetrahydro-1H-3-aza-acenaphthylen-3-yl)-propyl]-ethyl-amide hydrochloride | | 496 |
| 121 | 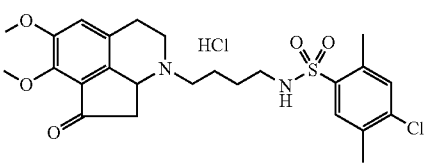 | 4-Chloro-N-[4-(7,8-dimethoxy-1-oxo-2,2a,4,5-tetrahydro-1H-3-aza-acenaphthylen-3-yl)-butyl]-2,5-dimethyl-benzenesulfonamide hydrochloride | 1H NMR (300 MHz, DMSO-d₆) δ ppm 1.44 (m, 2 H) 1.70 (m, 2 H) 2.34 (s, 3 H) 2.51 (s, 3 H) 2.78 (m, 2 H) 3.07 (m, 6 H)) 3.43 (m, 2 H) 3.82 (s, 3 H) 3.87 (s, 3 H) 4.72 (m, 1 H) 7.30 (s, 1 H) 7.51 (s, 1 H) 7.76 (s, 1 H) 7.82 (m, 1 H) 10.66 (br, 1 H) | 507 |
| 122 | 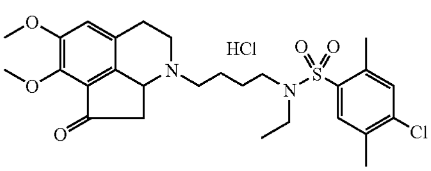 | 4-Chloro-N-[4-(7,8-dimethoxy-1-oxo-2,2a,4,5-tetrahydro-1H-3-aza-acenaphthylen-3-yl)-butyl]-N-ethyl-2,5-dimethyl-benzenesulfonamide hydrochloride | | 535 |

-continued

| N° | STRUCTURE | Autonom | ¹H-NMR | MS (APCI (M + H)⁺) |
|---|---|---|---|---|
| 123 | 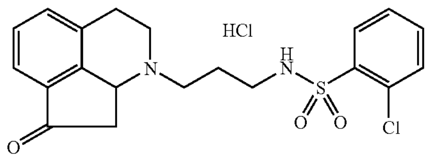 | 2-Chloro-N-[3-(1-oxo-2,2a,4,5-tetrahydro-1H-3-aza-acenaphthylen-3-yl)-propyl]-benzenesulfonamide hydrochloride | | 405 |
| 124 | 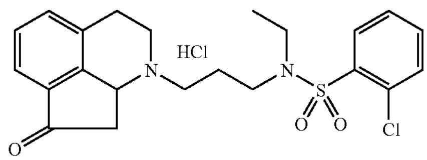 | 2-Chloro-N-ethyl-N-[3-(1-oxo-2,2a,4,5-tetrahydro-1H-3-aza-acenaphthylen-3-yl)-propyl]-benzenesulfonamide hydrochloride | | 433 |
| 125 | 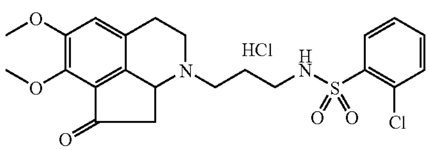 | 2-Chloro-N-[3-(7,8-dimethoxy-1-oxo-2,2a,4,5-tetrahydro-1H-3-aza-acenaphthylen-3-yl)-propyl]-benzenesulfonamide hydrochloride | | 465 |
| 126 | 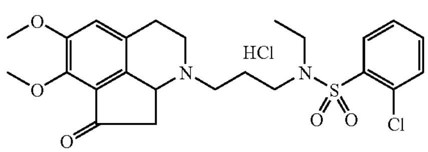 | 2-Chloro-N-[3-(7,8-dimethoxy-1-oxo-2,2a,4,5-tetrahydro-1H-3-aza-acenaphthylen-3-yl)-propyl]-N-ethyl-benzenesulfonamide hydrochloride | | 493 |
| 127 | 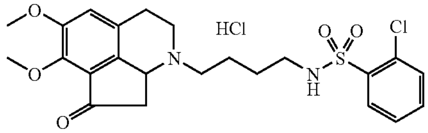 | 2-Chloro-N-[4-(7,8-dimethoxy-1-oxo-2,2a,4,5-tetrahydro-1H-3-aza-acenaphthylen-3-yl)-butyl]-benzenesulfonamide hydrochloride | 1H NMR (300 MHz, DMSO-d₆) δ ppm 1.47 (m, 2 H) 1.73 (m, 2 H) 2.86 (m, 2 H) 3.10 (m, 6 H) 3.45 (m, 2 H) 3.82 (s, 3 H) 3.87 (s, 3 H) 4.72 (m, 1 H) 7.30 (s, 1 H) 7.54 (m, 1 H) 7.66 (m, 2 H) 7.98 (m, 2 H) 10.80 (br, 1 H) | 479 |
| 128 | 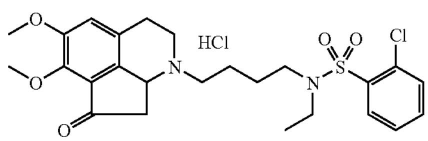 | 2-Chloro-N-[4-(7,8-dimethoxy-1-oxo-2,2a,4,5-tetrahydro-1H-3-aza-acenaphthylen-3-yl)-butyl]-N-ethyl benzenesulfonamide hydrochloride | | 507 |
| 129 | 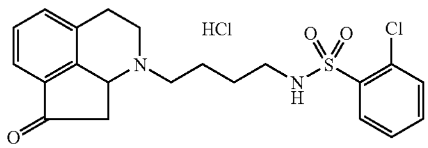 | 2-Chloro-N-[4-(1-oxo-2,2a,4,5-tetrahydro-1H-3-aza-acenaphthylen-3-yl)-butyl]-benzenesulfonamide hydrochloride | | 419 |
| 130 | 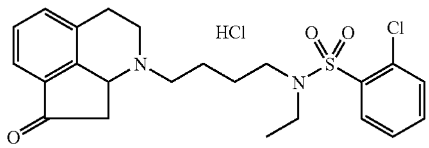 | 2-Chloro-N-ethyl-N-[4-(1-oxo-2,2a,4,5-tetrahydro-1H-3-aza-acenaphthylen-3-yl)-butyl]-benzenesulfonamide hydrochloride | | 447 |
| 131 | 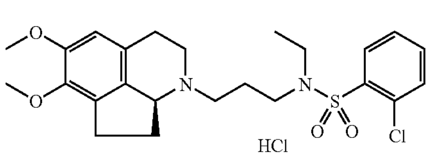 | (S)-2-Chloro-N-[3-(7,8-dimethoxy-2,2a,4,5-tetrahydro-1H-3-aza-acenaphthylen-3-yl)-propyl]-N-ethyl-benzenesulfonamide hydrochloride | | 479 |

-continued

| N° | STRUCTURE | Autonom | ¹H-NMR | MS (APCI (M + H)⁺) |
|---|---|---|---|---|
| 132 | 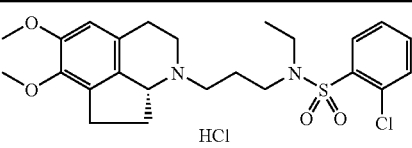 | (R)-2-Chloro-N-[3-(7,8-dimethoxy-2,2a,4,5-tetrahydro-1H-3-aza-acenaphthylen-3-yl)-propyl]-N-ethyl-benzenesulfonamide hydrochloride | | 479 |
| 133 | 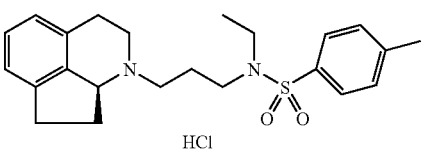 | (S)-N-Ethyl-4-methyl-N-[3-(2,2a,4,5-tetrahydro-1H-3-aza-acenaphthylen-3-yl)-propyl]-benzenesulfonamide hydrochloride | | 399 |
| 134 | 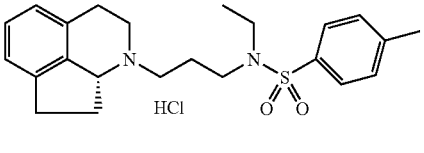 | (R)-N-Ethyl-4-methyl-N-[3-(2,2a,4,5-tetrahydro-1H-3-aza-acenaphthylen-3-yl)-propyl]-benzenesulfonamide hydrochloride | | 399 |
| 135 | 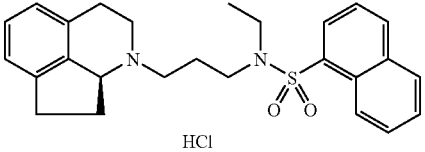 | (S)-Naphthalene-1-sulfonic acid ethyl-[3-(2,2a,4,5-tetrahydro-1H-3-aza-acenaphthylen-3-yl)-propyl]-amide hydrochloride | | 435 |
| 136 | 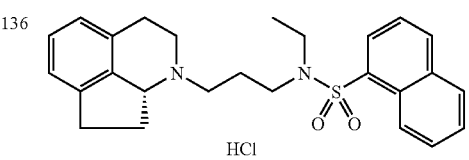 | (R)-Naphthalene-1-sulfonic acid ethyl-[3-(2,2a,4,5-tetrahydro-1H-3-aza-acenaphthylen-3-yl)-propyl]-amide hydrochloride | | 435 |

Biological Assays

Radioligand Binding

Radioligand binding assays were performed using the Cloned Human Serotonin Receptor, Subtype 7 (h5HT$_7$), expressed in CHO cells, coated on Flashplate (Basic Flash-Plate Cat.: SMP200) from PerkinElmer (Cat.: 6120512). The protocol assay was essentially the recommended protocol in the Technical Data Sheet by PerkinEmer Life and Analytical Sciences. The Mass membrane protein/well was typically 12 µg and the Receptor/well was about 9-10 fmoles. The Flashplate were let equilibrate at room temperature for one hour before the addition of the components of the assay mixture. The binding buffer was: 50 mM Tris-HCl, pH 7.4, containing 10 mM MgCl$_2$, 0.5 mM EDTA and 0.5% BSA. The radioligand was [$^{125}$I]LSD at a final concentration of 0.82 nM. Nonspecific binding was determined with 50 µM of Clozapine. The assay volume was 25 µl. TopSeal-A were applied onto Flashplate microplates and they were incubated at room temperature for 240 minutes in darkness. The radioactivity were quantified by liquid scintillation spectrophotometry (Wallac 1450 Microbeta Trilux) with a count delay of 4 minutes prior to counting and a counting time of 30 seconds per well. Competition binding data were analyzed by using the LIGAND program (Munson and Rodbard, LIGAND: A versatile, computerized approach for characterization of ligand-binding systems. *Anal. Biochem.* 107: 220-239, 1980) and assays were performed in triplicate determinations for each point. Results for representative compounds are given in the table 2 below:

TABLE 2

| COMPOUND | 5-HT7 IC-50 (nM) |
|---|---|
| 7 | 79.2 |
| 15 | 142.1 |
| 56 | 155.6 |
| 58 | 188.5 |
| 80 | 6.2 |
| 87 | 20.3 |
| 88 | 4.5 |
| 89 | 6.7 |
| 111 | 8.0 |

The invention claimed is:

1. A compound of the formula I:

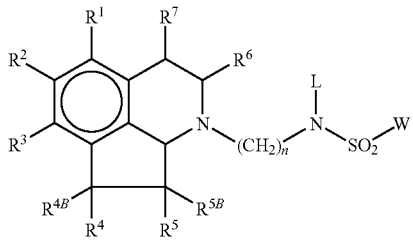

(I)

wherein
- W is a substituted or unsubstituted alkyl, substituted or unsubstituted alkenyl, substituted or unsubstituted cycloalkyl, substituted or unsubstituted aryl, substituted or unsubstituted heterocyclyl;
- $R^1$, $R^2$, $R^3$, $R^4$, $R^{4B}$, $R^5$, $R^{5B}$, $R^6$ and $R^7$ are each independently selected from the group formed by hydrogen, substituted or unsubstituted alkyl, substituted or unsubstituted cycloalkyl, substituted or unsubstituted alkenyl, substituted or unsubstituted aryl, substituted or unsubstituted heterocyclyl, —$COR^8$, —$C(O)OR^8$, —$C(O)NR^8R^9$, —$HC=NR^8$, —CN, —$OR^8$, —$OC(O)R^8$, —$S(O)_t$—$R^8$, —$NR^8R^9$, —$NR^8C(O)R^9$, —$NO_2$, —$N=CR^8R^9$ or halogen;
- L is hydrogen, substituted or unsubstituted alkyl, substituted or unsubstituted cycloalkyl, substituted or unsubstituted alkenyl, substituted or unsubstituted aryl, substituted or unsubstituted heterocyclyl, —$COR^8$, —$C(O)OR^8$, —$C(O)NR^8R^9$, —$HC=NR^8$, —CN, —$OR^8$, —$OC(O)R^8$, —$S(O)_t$—$R^8$, —$NR^8R^9$, —$NR^8C(O)R^9$, or —$N=CR^8R^9$; and wherein the pair $R^4$ and $R^{4B}$ or the pair $R^5$ and $R^{5B}$ taken together may form a carbonyl group,
- t is 1, 2 or 3;
- $R^8$ and $R^9$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, halogen;
- n is 2, 3, 4 or 5;

or a pharmaceutically acceptable salt, isomer, prodrug or solvate thereof.

2. A compound according to claim 1 characterized in that n is 3 or 4.

3. A compound according to claim 1 characterized in that W is an aromatic group selected from substituted or unsubstituted aryl, substituted or unsubstituted heterocyclyl, or substituted or unsubstituted phenyl.

4. A compound according to claim 3 characterized in that W is selected from alkyl, alkoxy and/or halo substituted phenyl.

5. A compound according to claim 1 characterized in that $R^5$, $R^{5B}$, $R^6$ and $R^7$ are H.

6. A compound according to claim 1 characterized in that $R^1$, $R^4$, $R^{4B}$, $R^5$ and $R^{5B}$ are H or in that $R^1$, $R^5$ and $R^{5B}$ are H and $R^4$ and $R^{4B}$ taken together form a carbonyl group.

7. A compound according to claims 5 or 6 wherein $R^2$ and $R^3$ are alkoxy, or in that $R^2$ is alkoxy and $R^3$ is H.

8. A process for the preparation of a compound of formula (I) or a salt, isomer or solvate thereof as claimed in claim 1, which comprises the coupling of a compound of Formula (II):

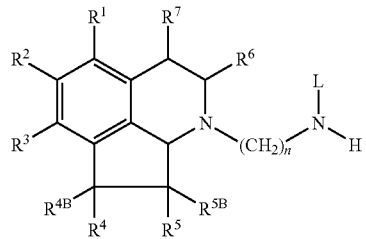

(II)

in which R1-R7 and n are as defined in Formula (I), with a compound of Formula (III):

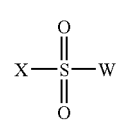

(III)

in which W is as defined in Formula (I) and X is an halogen, preferably Cl.

9. A pharmaceutical composition which comprises a compound as defined in claim 1 or a pharmaceutically acceptable salt, prodrug, isomer or solvate thereof, and a pharmaceutically acceptable carrier, adjuvant or vehicle.

10. A pharmaceutical composition according to claim 9 for oral administration.

11. A compound according to claim 2 characterized in that W is an aromatic group selected from substituted or unsubstituted aryl, substituted or unsubstituted heterocyclyl, or substituted or unsubstituted phenyl.

12. A compound according to claim 11 characterized in that W is selected from alkyl, alkoxy and/or halo substituted phenyl.

13. A compound according to claim 2 characterized in that $R^5$, $R^{5B}$, $R^6$ and $R^7$ are H.

14. A compound according to claim 3 characterized in that $R^5$, $R^{5B}$, $R^6$ and $R^7$ are H.

15. A compound according to claim 4 characterized in that $R^5$, $R^{5B}$, $R^6$ and $R^7$ are H.

16. A compound according to claim 11 characterized in that $R^5$, $R^{5B}$, $R^6$ and $R^7$ are H.

17. A compound according to claim 12 characterized in that $R^5$, $R^{5B}$, $R^6$ and $R^7$ are H.

18. A compound according to claim 2 characterized in that $R^1$, $R^4$, $R^{4B}$, $R^5$ and $R^{5B}$ are H or in that $R^1$, $R^5$ and $R^{5B}$ are H and $R^4$ and $R^{4B}$ taken together form a carbonyl group.

19. A compound according to claim 3 characterized in that $R^1$, $R^4$, $R^{4B}$, $R^5$ and $R^{5B}$ are H or in that $R^1$, $R^5$ and $R^{5B}$ are H and $R^4$ and $R^{4B}$ taken together form a carbonyl group.

20. A compound according to claim 4 characterized in that $R^1$, $R^4$, $R^{4B}$, $R^5$ and $R^{5B}$ are H or in that $R^1$, $R^5$ and $R^{5B}$ are H and $R^4$ and $R^{4B}$ taken together form a carbonyl group.

21. A compound according to claim 5 characterized in that $R^1$, $R^4$, $R^{4B}$, $R^5$ and $R^{5B}$ are H or in that $R^1$, $R^5$ and $R^{5B}$ are H and $R^4$ and $R^{4B}$ taken together form a carbonyl group.

22. A compound according to claim 11 characterized in that $R^1$, $R^4$, $R^{4B}$, $R^5$ and $R^{5B}$ are H or in that $R^1$, $R^5$ and $R^{5B}$ are H and $R^4$ and $R^{4B}$ taken together form a carbonyl group.

23. A compound according to claim 12 characterized in that $R^1$, $R^4$, $R^{4B}$, $R^5$ and $R^{5B}$ are H or in that $R^1$, $R^5$ and $R^{5B}$ are H and $R^4$ and $R^{4B}$ taken together form a carbonyl group.

24. A compound according to claim 13 characterized in that $R^1$, $R^4$, $R^{4B}$, $R^5$ and $R^{5B}$ are H or in that $R^1$, $R^5$ and $R^{5B}$ are H and $R^4$ and $R^{4B}$ taken together form a carbonyl group.

25. A compound according to claim 14 characterized in that $R^1$, $R^4$, $R^{4B}$, $R^5$ and $R^{5B}$ are H or in that $R^1$, $R^5$ and $R^{5B}$ are H and $R^4$ and $R^{4B}$ taken together form a carbonyl group.

26. A compound according to claim 15 characterized in that $R^1$, $R^4$, $R^{4B}$, $R^5$ and $R^{5B}$ are H or in that $R^1$, $R^5$ and $R^{5B}$ are H and $R^4$ and $R^{4B}$ taken together form a carbonyl group.

27. A compound according to claim 12 characterized in that $R^1$, $R^4$, $R^{4B}$, $R^5$ and $R^{5B}$ are H or in that $R^1$, $R^5$ and $R^{5B}$ are H and $R^4$ and $R^{4B}$ taken together form a carbonyl group.

28. A compound according to claim 13 characterized in that $R^1$, $R^4$, $R^{4B}$, $R^5$ and $R^{5B}$ are H or in that $R^1$, $R^5$ and $R^{5B}$ are H and $R^4$ and $R^{4B}$ taken together form a carbonyl group.

29. A compound according to claim 5 wherein $R^2$ and $R^3$ are methoxy, or in that $R^2$ is methoxy and $R^3$ is H.

30. A compound according to claim 6 wherein $R^2$ and $R^3$ are methoxy, or in that $R^2$ is methoxy and $R^3$ is H.

* * * * *